(12) United States Patent
Kim et al.

(10) Patent No.: US 8,673,460 B2
(45) Date of Patent: Mar. 18, 2014

(54) HETEROCYCLIC DERIVATIVE AND ORGANIC LIGHT EMITTING DEVICE USING SAME

(75) Inventors: Ji-Eun Kim, Daejeon (KR); Kong-Kyeom Kim, Daejeon (KR); Se-Hwan Son, Daejeon (KR); Jun-Gi Jang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 13/259,966

(22) PCT Filed: Sep. 10, 2010

(86) PCT No.: PCT/KR2010/006167
§ 371 (c)(1),
(2), (4) Date: Sep. 23, 2011

(87) PCT Pub. No.: WO2011/031086
PCT Pub. Date: Mar. 17, 2011

(65) Prior Publication Data
US 2012/0161612 A1     Jun. 28, 2012

(30) Foreign Application Priority Data
Sep. 10, 2009 (KR) .................. 10-2009-0085474

(51) Int. Cl.
*H01L 51/54* (2006.01)

(52) U.S. Cl.
USPC ........... 428/690; 428/917; 313/504; 313/505; 313/506; 257/40; 257/E51.026; 257/E51.05; 564/26; 564/426; 564/434; 548/418; 548/440

(58) Field of Classification Search
USPC .................. 428/690, 917; 313/504, 505, 506; 257/40, E51.026, E51.05; 564/26, 426, 564/434; 548/418, 440
See application file for complete search history.

(56) References Cited

U.S. PATENT DOCUMENTS

| 2001/0015614 A1* | 8/2001 | Taguchi | 313/483 |
| 2004/0170863 A1* | 9/2004 | Kim et al. | 428/690 |

FOREIGN PATENT DOCUMENTS

| JP | 2000-311787 | 11/2000 |
| JP | 2001-172280 | 6/2001 |
| KR | 10-2008-0028424 | 3/2008 |
| WO | WO 2006-050007 | 5/2006 |

* cited by examiner

*Primary Examiner* — Gregory Clark
(74) *Attorney, Agent, or Firm* — McKenna Long & Aldridge LLP

(57) ABSTRACT

The present invention relates to a novel heterocyclic derivative and an organic light emitting device using the compound, and the heterocyclic derivative may largely improve a life span, efficiency, electrochemical stability and thermal stability of the organic light emitting device.

10 Claims, 1 Drawing Sheet

HETEROCYCLIC DERIVATIVE AND ORGANIC LIGHT EMITTING DEVICE USING SAME

This application is a National Stage Application of PCT/KR2010/006167, filed on Sep. 10, 2010, which claims priority to Korean Patent Application No. 10-2009-0085474, filed on Sep. 10, 2009, the disclosure of which is incorporated herein by reference in its entirety.

TECHNICAL FIELD

The present invention relates to a novel compound and an organic light emitting device using the same.

BACKGROUND ART

An organic light emission phenomenon is an example of a conversion of current into visible rays through an internal process of a specific organic molecule. The organic light emission phenomenon is based on the following mechanism. When an organic material layer is disposed between an anode and a cathode, if voltage is applied between two electrodes, electrons and holes are injected from the cathode and the anode to the organic material layer. The electrons and the holes which are injected into the organic material layer are recombined to form an exciton, and the exciton is reduced to a bottom state to emit light. In general, the organic light emitting device using this principle may be configured by a cathode, an anode, and an organic material layer disposed therebetween, for example, an organic material layer including a hole injection layer, a hole transport layer, a light emitting layer, and an electron transport layer.

The materials used in the organic light emitting device are mostly pure organic materials or complexes of organic material and metal. The material used in the organic light emitting device may be classified into a hole injection material, a hole transport material, a light emitting material, an electron transport material, or an electron injection material, according to its use. In connection with this, an organic material having a p-type property, which is easily oxidized and is electrochemical stable when it is oxidized, is mostly used as the hole injection material or the hole transport material. Meanwhile, an organic material having an n-type property, which is easily reduced and is electrochemical stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further has the following properties.

First, it is preferable that the material used in the organic light emitting device has excellent thermal stability. The reason is that joule heat is generated by movement of electric charges in the organic light emitting device. NPB, which has recently been used as the hole transport layer material, has a glass transition temperature of 100° C. or lower, thus it has difficulty in being applied to an organic light emitting device requiring a high current.

Second, in order to produce an organic light emitting device that is capable of being actuated at low voltage and has high efficiency, holes or electrons which are injected into the organic light emitting device must be smoothly transported to a light emitting layer, and the injected holes and electrons must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long life span.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode including metal or metal oxides so as to assure stability of the device.

DISCLOSURE

Technical Problem

The present invention has been made in an effort to provide a novel heterocyclic derivative that can satisfy conditions required in the material used in an organic light emitting device, for example, an appropriate energy level, electrochemical stability and thermal stability, and has a chemical structure that can perform various roles required in the organic light emitting device according to a substituent group, and an organic light emitting device using the same.

Technical Solution

An exemplary embodiment of the present invention provides a compound represented by the following Formula 1:

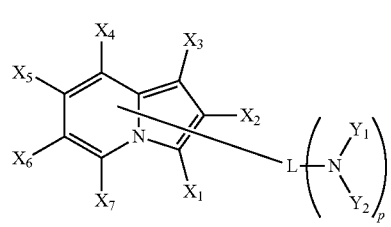

[Formula 1]

wherein

L is a connection group connected to at least one A, and substituted or unsubstituted $C_6$ to $C_{60}$ arylene group, substituted or unsubstituted fluorene group, or substituted or unsubstituted $C_3$ to $C_{60}$ heteroarylene group, $Y_1$ and $Y_2$ are the same as or different from each other, and each independently substituted or unsubstituted $C_6$ to $C_{60}$ aryl group, or substituted or unsubstituted $C_3$ to $C_{60}$ heteroaryl group, p is an integer in the range of 1 to 10, at least one of $X_1$ to $X_7$ is connected to L, and the remains are each independently hydrogen; deuterium; halogen; cyano group; nitro group; hydroxyl group; substituted or unsubstituted $C_1$ to $C_{50}$ alkyl group; substituted or unsubstituted $C_1$ to $C_{50}$ alkoxy group; substituted or unsubstituted $C_3$ to $C_{50}$ cycloalkyl group; substituted or unsubstituted $C_3$ to $C_{60}$ heterocycloalkyl group; substituted or unsubstituted $C_6$ to $C_{60}$ aryl group; substituted or unsubstituted $C_3$ to $C_{60}$ heteroaryl group; substituted or unsubstituted arylamine group; or substituted or unsubstituted silicon group.

Another exemplary embodiment of the present invention provides an organic light emitting device comprising a first electrode, one or more organic material layers including a light emitting layer, and a second electrode in a layer form, wherein one or more layers of the organic material layers include the compound of Formula 1.

Advantageous Effects

A compound according to the present invention may be used as an organic material layer material, particularly, a light emitting material, a hole injection material and/or a hole transport material in an organic light emitting diode, and in the case of using the compound in the organic light emitting device, driving voltage of the device is lowered, light efficiency is improved, and a life span property of the device is improved because of thermal stability of the compound.

The light emitting layer of the organic light emitting device according to the exemplary embodiment of the present invention may include red, green, blue or white phosphorescent or fluorescent dopant. Among them, the phosphorescent dopant may be an organic metal compound that includes one or more elements that are selected from the group consisting of Ir, Pt, Os, Ti, Zr, Hf, Eu, Tb and Tm.

BEST MODE FOR CARRYING OUT THE INVENTION

Figure 1:
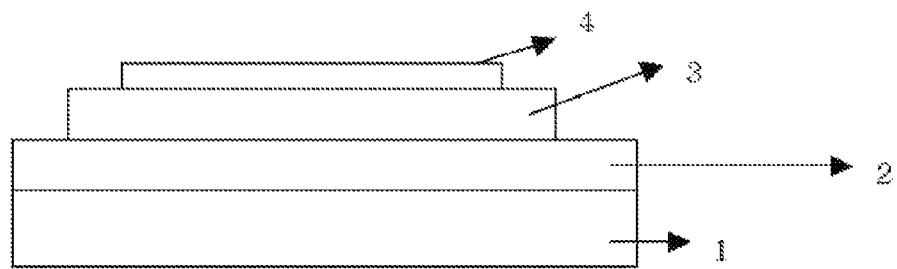
FIG. 1 illustrates an example of an organic light emitting device that includes a substrate (1), an anode (2), a light emitting layer (3), and a cathode (4).

Hereinafter, the present invention will be described in detail.

A compound according to an exemplary embodiment of the present invention is represented by Formula 1.

In Formula 1, the aryl group may be a monocycle or a polycycle, and the number of carbon atoms is not particularly limited, but it is preferable that it is in the range of 6 to 60. Examples of the monocyclic aryl group include phenyl group, biphenyl group, terphenyl group, stilben and the like, and examples of the polycyclic aryl group include naphthyl group, anthracenyl group, phenanthrene group, pyrenyl group, perylenyl group, cryxenyl group and the like, but the scope of the exemplary embodiment of the present invention is not limited thereto.

In Formula 1, the heterocyclic group such as heterocycloalkyl group or heteroaryl group is a cyclic group including O, N or S as a heteroatom, and the number of carbon atoms is not particularly limited but preferably 3 to 60. Examples of the heteroaryl group include thiophene group, furan group, pyrrole group, imidazole group, thiazole group, oxazol group, oxadiazol group, triazol group, pyridyl group, pyradazine group, quinolinyl group, isoquinoline group, or acridly group, but are not limited thereto.

In Formula 1, the following heterocyclic groups are preferable as the substituted or unsubstituted heteroarylene group, but it is not limited thereto.

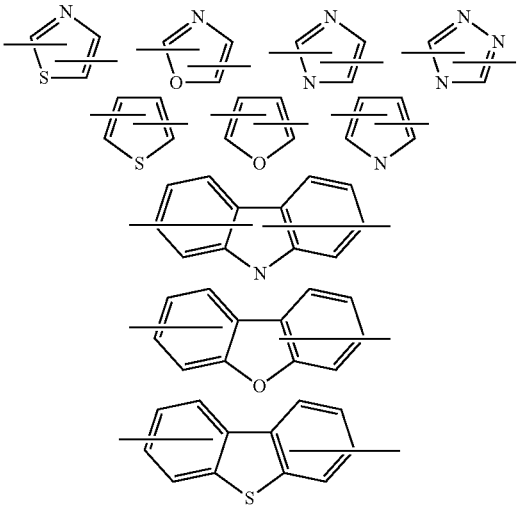

In Formula 1,

is preferably the following groups, but is not limited thereto.

1

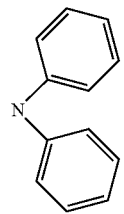

2

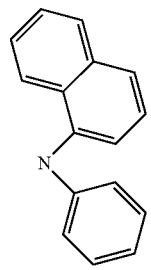

3

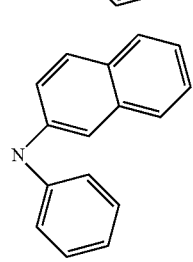

-continued
4
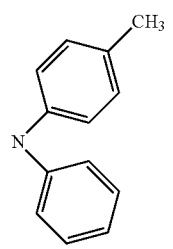
5
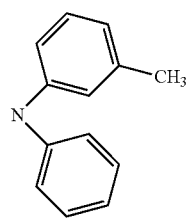
6
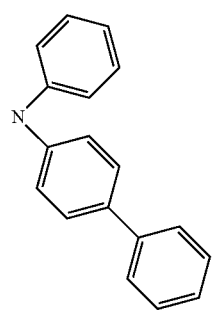
7
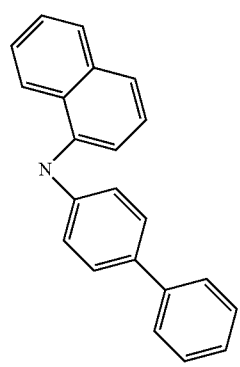
8
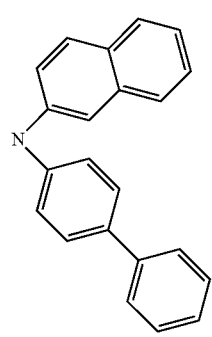
-continued
9
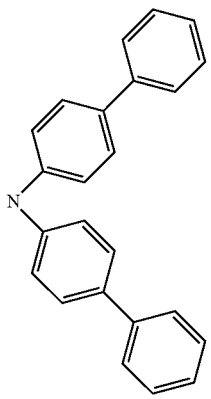
10
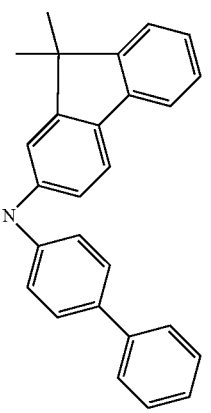
11
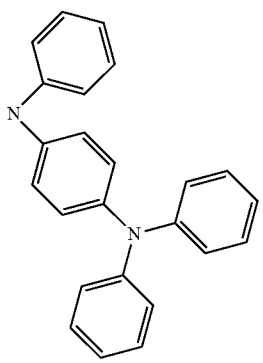
12
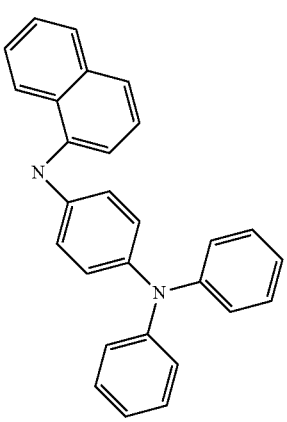

13
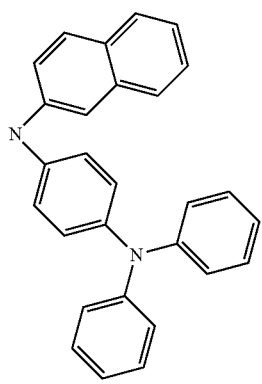
14
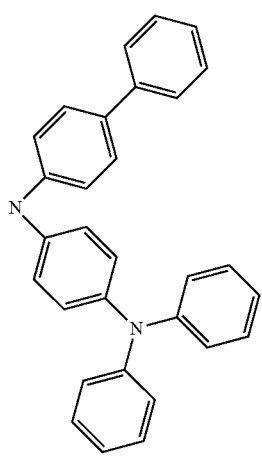
15
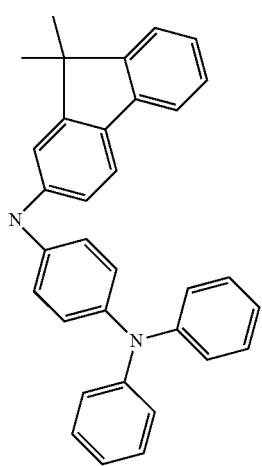
16
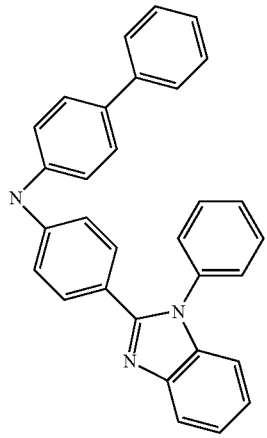
17
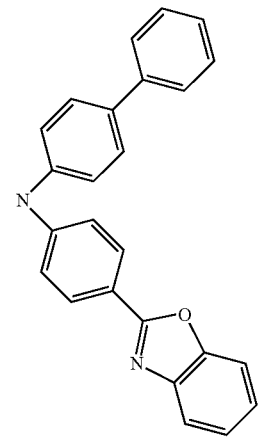
18
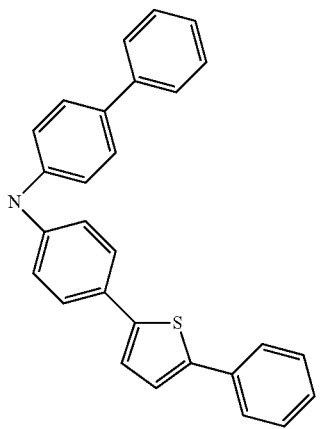
19
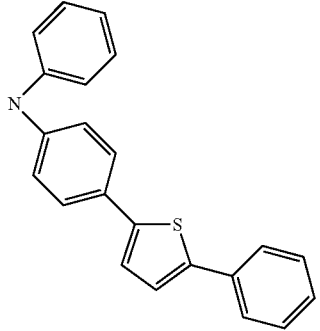

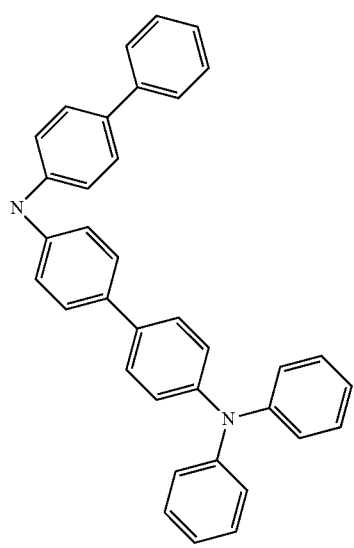
20
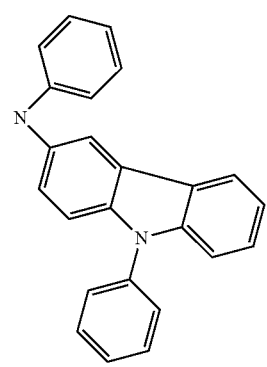
21
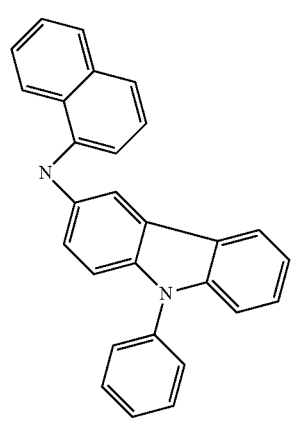
22
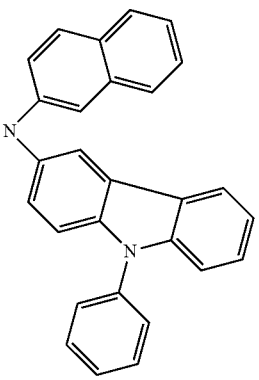
23
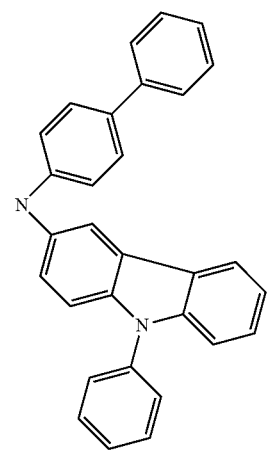
24
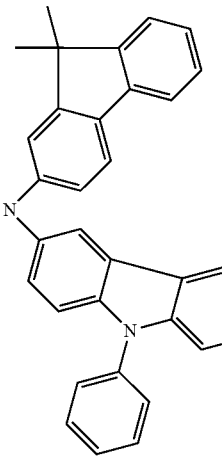
25
In Formula 1, the fluorene group is preferably the following structure, but is not limited thereto.
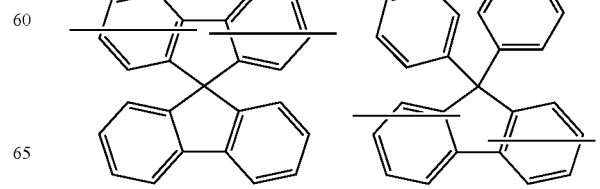

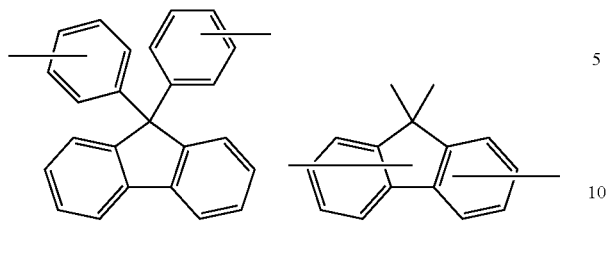

In Formula 1, the alkyl group or alkoxy group includes a straight or branched chain.

In Formula 1, "substituted or unsubstituted" means that it is substituted or unsubstituted by at least one substituent group that is selected from the group consisting of deuterium; halogen; cyano group; nitro group; hydroxyl group; $C_1$ to $C_{50}$ alkyl group; $C_1$ to $C_{50}$ alkoxy group; $C_3$ to $C_{50}$ cycloalkyl group; $C_3$ to $C_{60}$ heterocycloalkyl group; $C_6$ to $C_{60}$ aryl group; $C_3$ to $C_{60}$ heteroaryl group; arylamine group; fluorene group; and silicon group.

According to an exemplary embodiment of the present invention, it is preferable that $X_1$ is connected to L, and $X_2$ is aryl group.

According to another exemplary embodiment of the present invention, it is preferable that $X_1$ is connected to L, and $X_2$ and $X_3$ are aryl group.

According to an exemplary embodiment of the present invention, it is preferable that $X_2$ is connected to L, and $X_1$ is aryl group.

According to another exemplary embodiment of the present invention, it is preferable that $X_2$ is connected to L, and $X_1$ and $X_3$ are aryl group.

A detailed example of the compound of Formula 1 may be a compound represented by the following Formulas, but is not limited thereto.

Formula 1-1

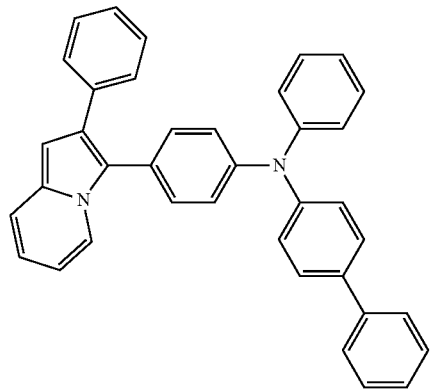

Formula 1-2

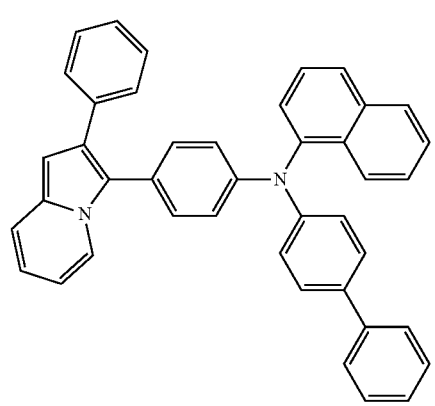

Formula 1-3

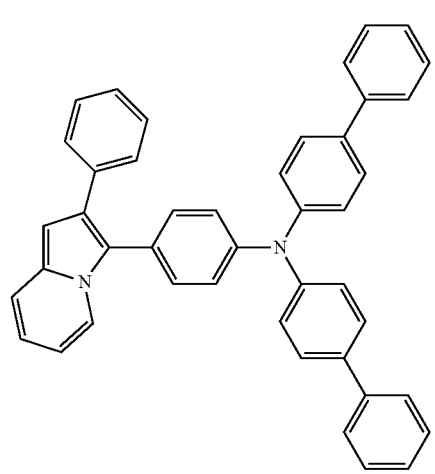

Formula 1-4

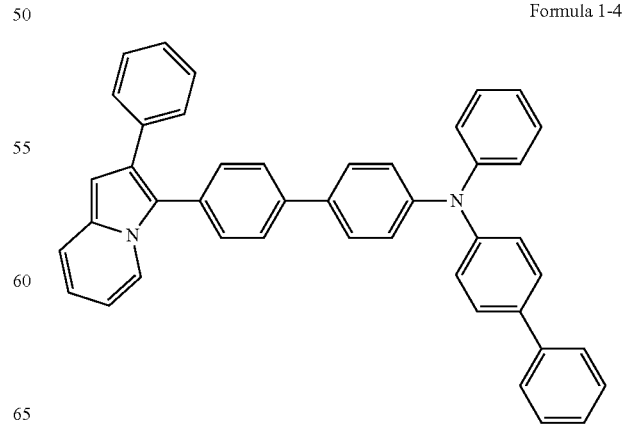

Formula 1-5
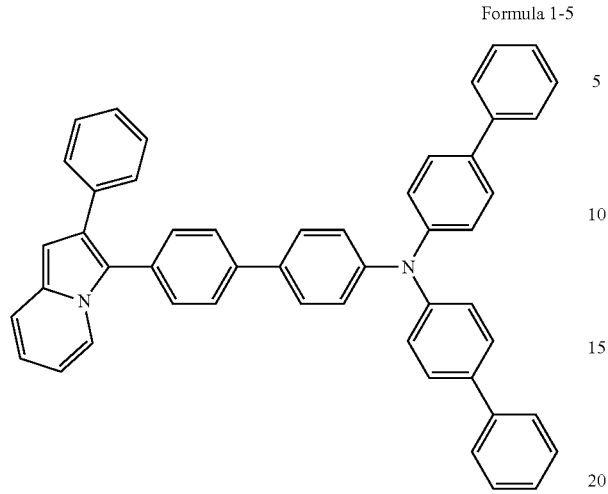
Formula 1-8
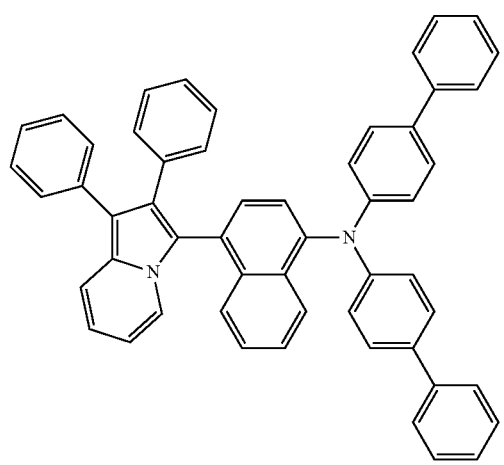
Formula 1-6
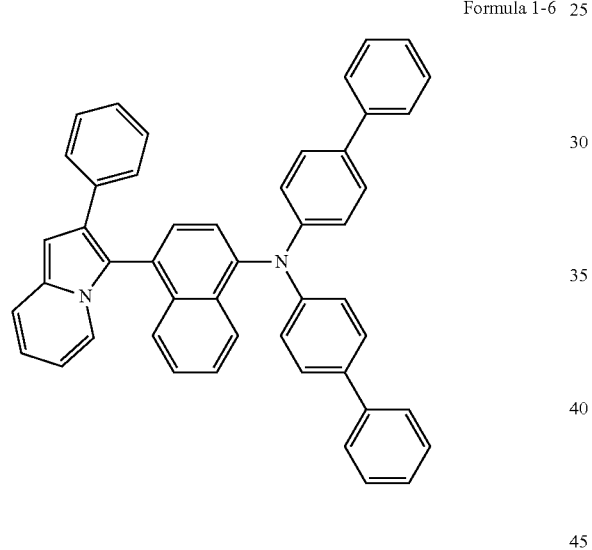
Formula 1-9
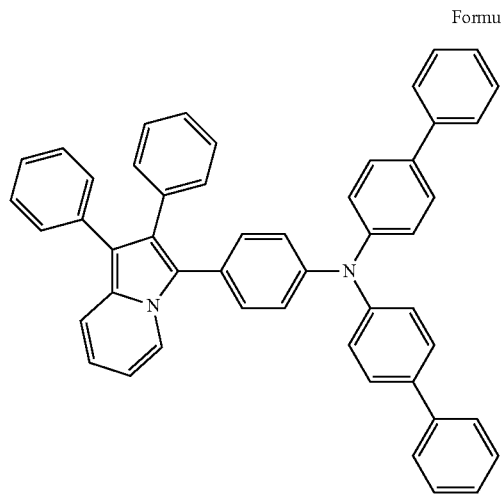
Formula 1-7
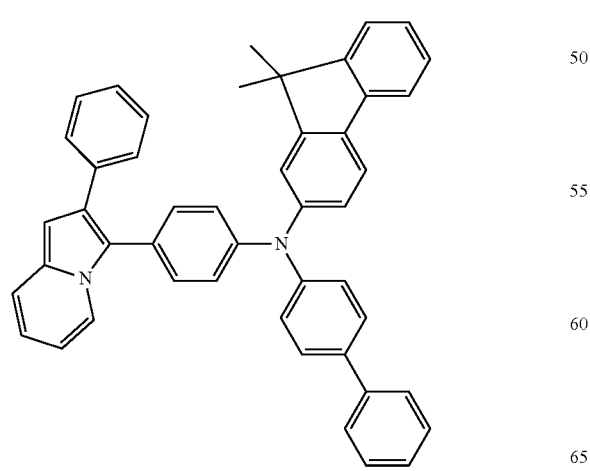
Formula 1-10
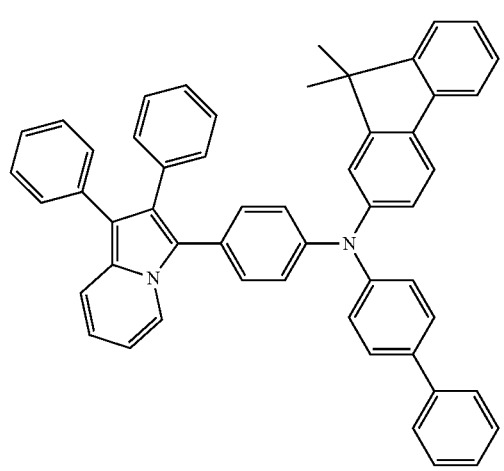

Formula 1-11
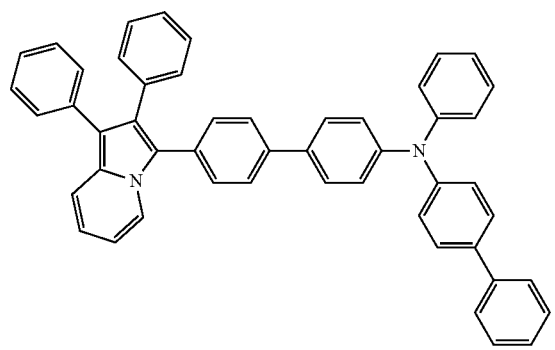
Formula 1-12
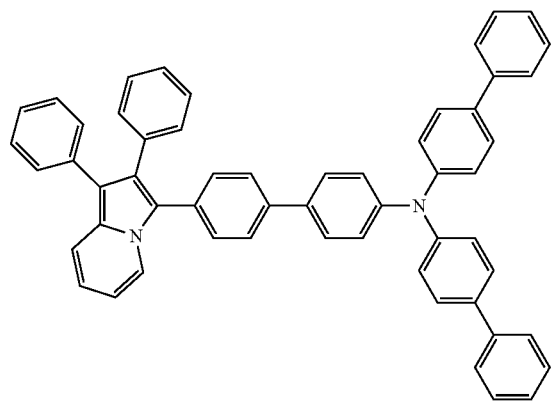
Formula 1-13
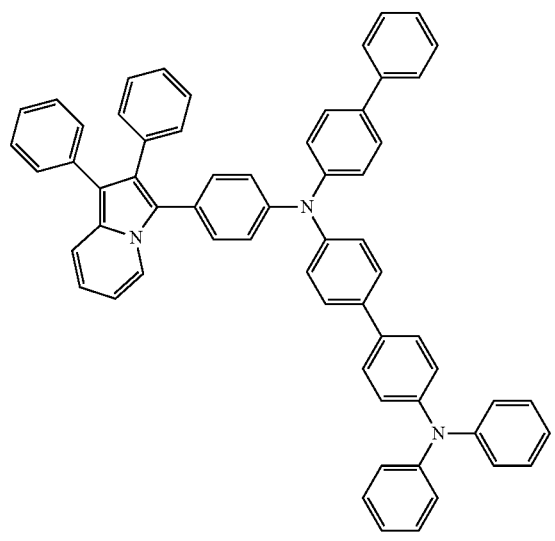
Formula 1-14
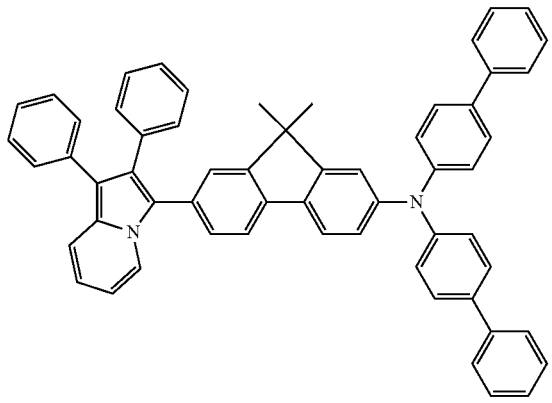
Formula 1-15
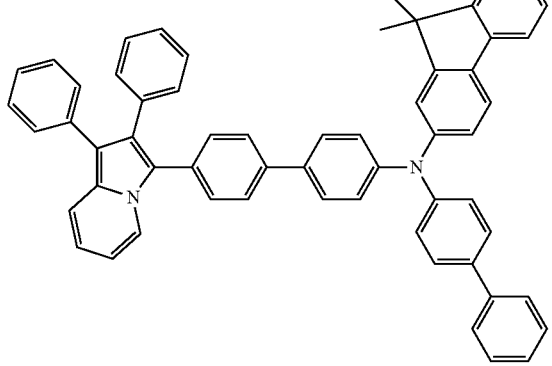
Formula 1-16
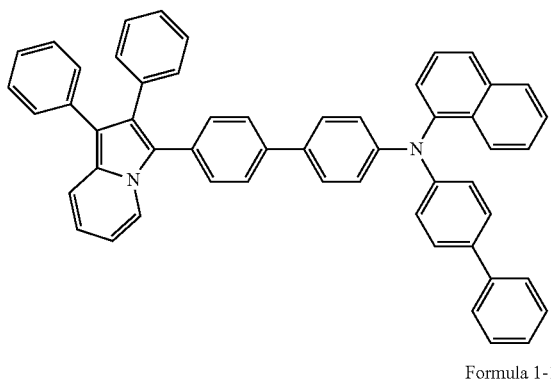
Formula 1-17
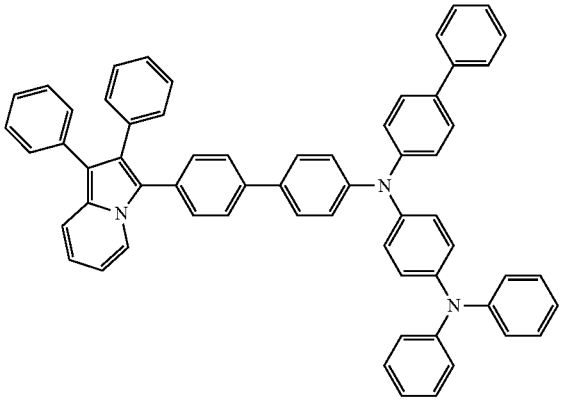

Formula 1-18
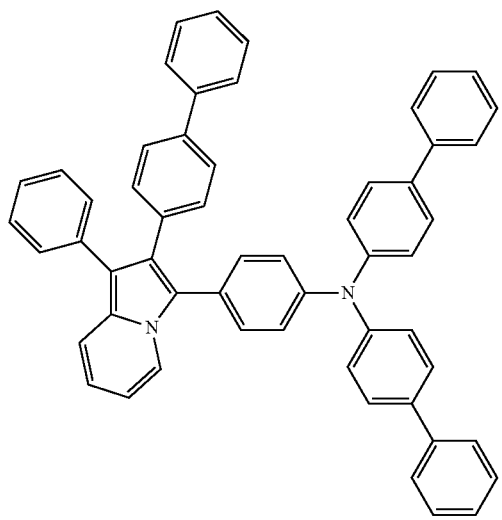
Formula 1-19
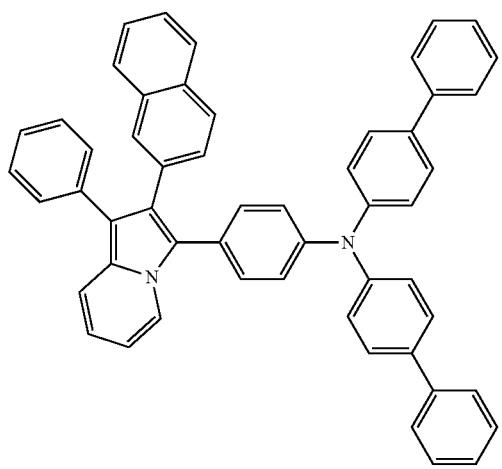
Formula 1-20
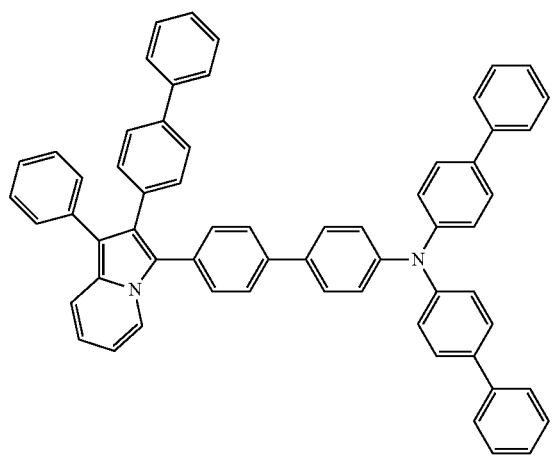
Formula 1-21
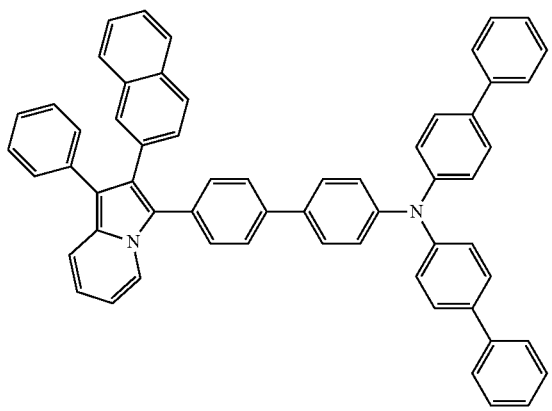
Formula 1-22
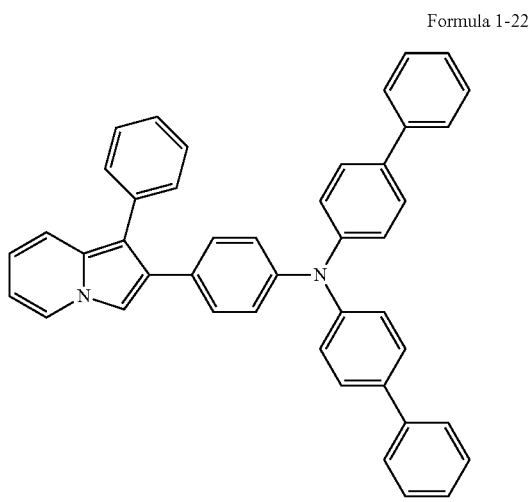
Formula 1-23
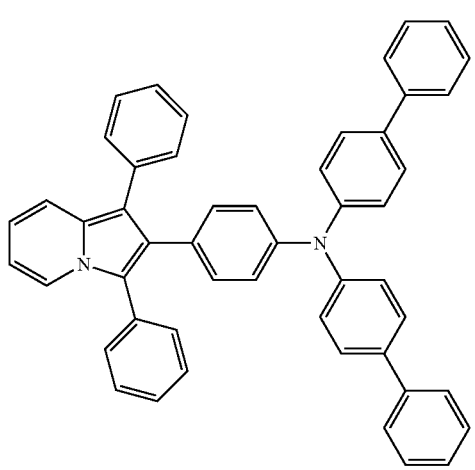

Formula 1-24
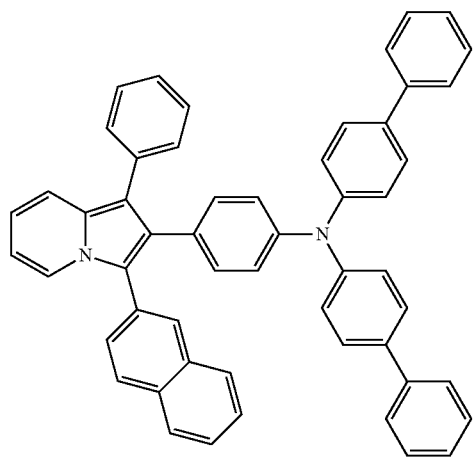
Formula 1-25
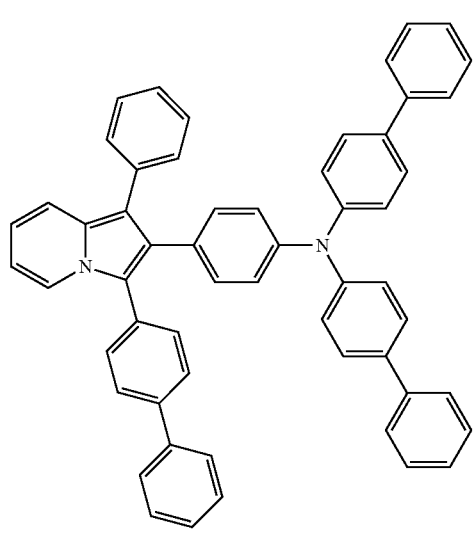
Formula 1-26
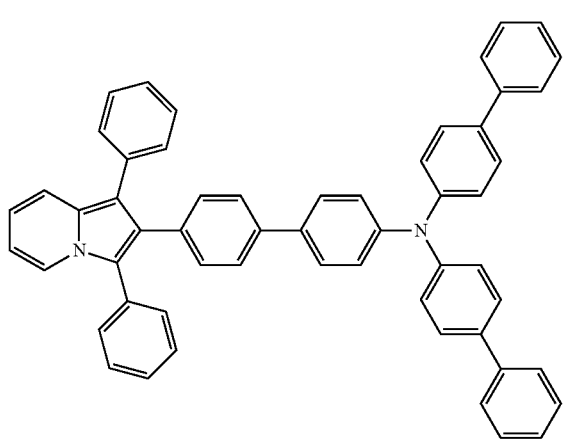
Formula 1-27
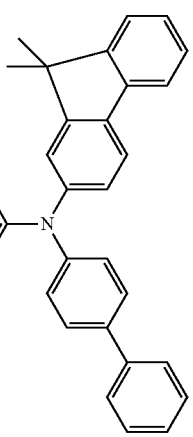
Formula 1-28
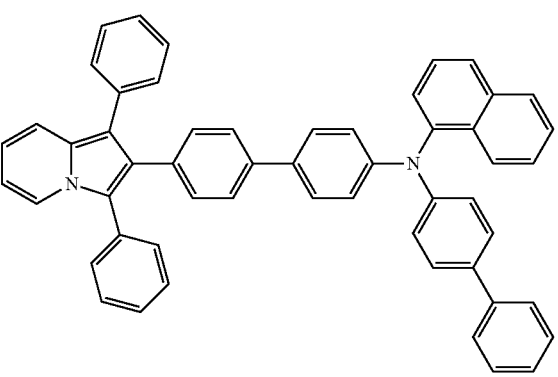
Formula 1-29
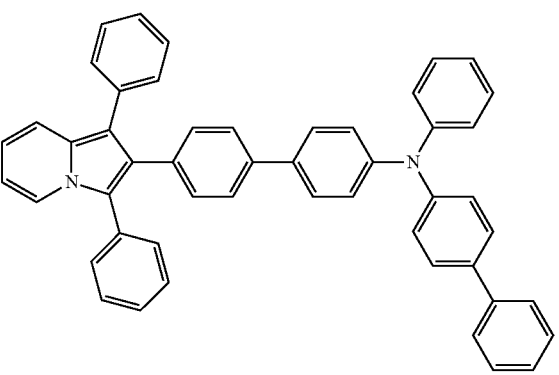
Formula 1-30

Formula 1-31

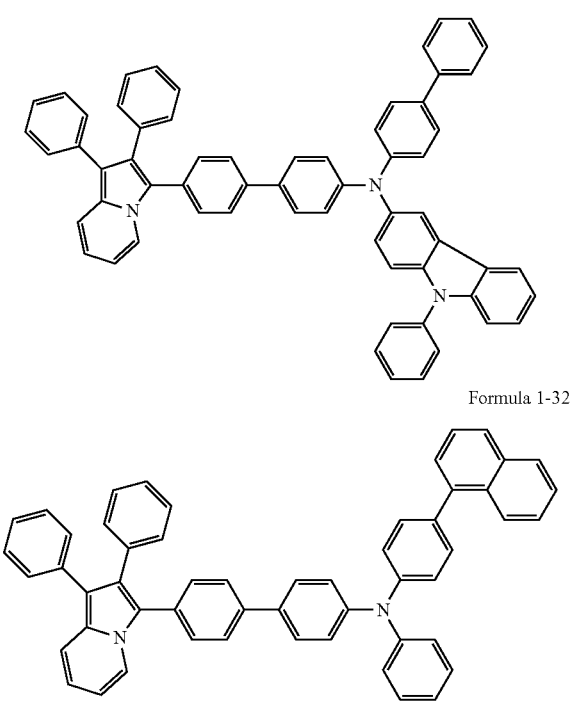

Formula 1-32

In addition, a general manufacturing method of the compound represented by Formula 1 will be described below.

First, Formula A is prepared like the following Reaction Equation 1.

[Reaction Equation 1]

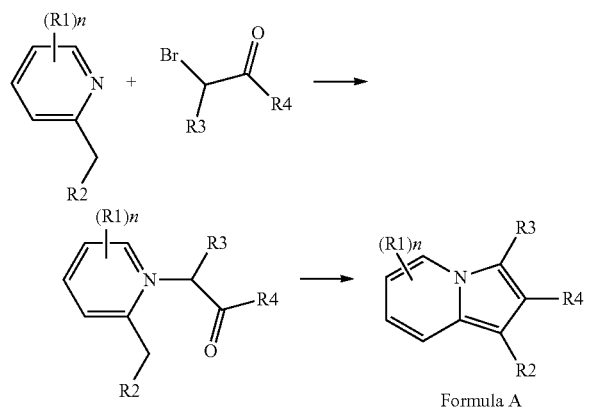

Formula A

In Reaction Equation 1, R1 to R4 are the same as the definitions of $X_1$ to $X_7$ of Formula 1, and n is an integer in the range of 1 to 4.

The compound represented by Formula 1 may be prepared by Suzuki coupling of Formula A made in Reaction Equation 1 under the presence of Pd catalyst, introduction of the amine group, and a brominating reaction.

The compound represented by Formula 1 according to the present invention can be manufactured with multistage chemical reactions. The preparation of the compounds will be described in the following Preparation Example. As shown in Preparation Example, some intermediate compounds are first manufactured, and the compounds represented by Formula 1 are manufactured from the intermediate compounds.

In addition, an organic electronic device according to the exemplary embodiment of the present invention includes a first electrode, a second electrode, and one or more organic material layers that are disposed between the first electrode and the second electrode, wherein one or more layers of the organic material layers include the compound that is represented by Formula 1.

The organic electronic device according to the present invention may be manufactured by using a manufacturing method and a material of a general organic electronic device, except that one or more organic material layers are formed by using the above compounds.

The compound that is represented by Formula 1 may be formed as the organic material layer by using a vacuum deposition method and a solution coating method when the organic electronic device is manufactured. In connection with this, illustrative, but non-limiting, examples of the solution coating process include a spin coating process, a dip coating process, an inkjet printing process, a screen printing process, a spray process, and a roll coating process.

The organic material layer of the organic electronic device according to the present invention may have a single layer structure, or a multilayered structure in which two or more organic material layers are layered. For example, the organic electronic device according to the exemplary embodiment of the present invention may have a structure including a hole injection layer, a hole transport layer, a light emitting layer, an electron transport layer, and an electron injection layer as the organic material layer. However, the structure of the organic electronic device is not limited to this, but may comprise the smaller number of organic material layers.

Therefore, in the organic electron device according to the exemplary embodiment of the present invention, the organic material layer may include the hole injection layer and the hole transport layer, and the hole injection layer or hole transport layer may include the compound represented by Formula 1.

In addition, the organic material layer may include a light emitting layer, and the light emitting layer may include the compound represented by Formula 1.

In the organic material layer having the multilayered structure, the compound represented by Formula 1 may form the organic material layer that can perform at least one role of light emitting, hole injection, hole transport, electron transport, electron injection roles. In particular, it is more preferable that the organic electronic device according to the exemplary embodiment of the present invention is included in the light emitting layer, the hole injection and/or transport layer or the layer that simultaneously performs light emitting and hole transport roles.

The light emitting layer of the organic light emitting device according to the exemplary embodiment of the present invention may include red, green, blue or white phosphorescent or fluorescent dopant. Among them, the phosphorescent dopant may be an organic metal compound that includes one or more elements that are selected from the group consisting of Ir, Pt, Os, Ti, Zr, Hf, Eu, Tb and Tm.

Figure 2:
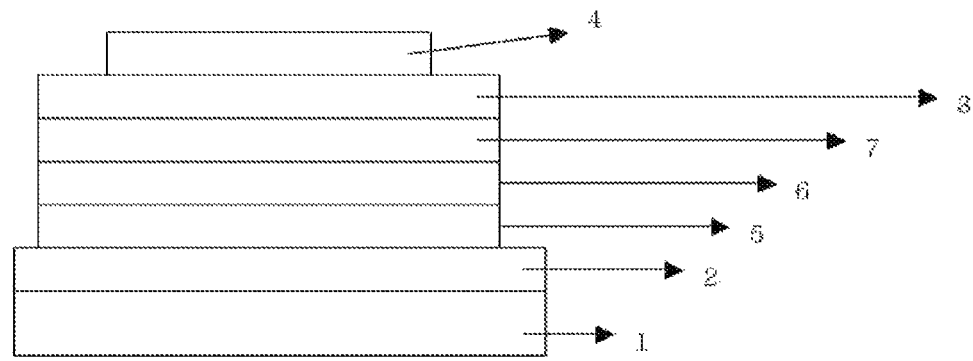
FIG. 2 illustrates an example of an organic light emitting device that includes a substrate (1), an anode (2), a hole injection layer (5), a hole transport layer (6), a light emitting layer (7), an electron transport layer (8), and a cathode (4).

For example, the structure of the organic light emitting device according to the present invention may have a structure shown in FIG. 1 or 2, but is not limited thereto.

FIG. 1 illustrates an example of an organic light emitting device that has a structure where a substrate (1), an anode (2), a light emitting layer (3), and a cathode (4) are sequentially layered. FIG. 2 illustrates an example of an organic light emitting device that includes a substrate (1), an anode (2), a hole injection layer (5), a hole transport layer (6), a light emitting layer (7), an electron transport layer (8), and a cathode (4).

FIGS. 1 and 2 illustrate a normal structure where the anode is disposed on the substrate, but are not limited thereto, and the exemplary embodiment of the present invention includes an inverted structure where the cathode is disposed on the substrate.

For example, the organic light emitting device according to the present invention may be manufactured by forming an anode by depositing metal or metal oxides having the conductivity or an alloy thereof on a substrate by using a PVD (physical vapor deposition) method such as sputtering or e-beam evaporation, forming the organic material layer that includes the hole injection layer, the hole transport layer, the light emitting layer and the electron transport layer thereon, and depositing the material that is capable of being used as a cathode thereon. In addition to this method, an organic light emitting device may be manufactured by sequentially depositing a cathode, an organic material layer, and an anode material on a substrate.

The organic material layer may have a multilayered structure that includes a hole injection layer, a hole transport layer, a light emitting layer, and an electron transport layer, but is not limited thereto and may have a single layer structure. The organic material layer may be manufactured in the smaller number of layers by using various polymer materials and by using not a deposition method but a solvent process, for example, spin coating, dip coating, doctor blading, screen printing, inkjet printing, heat transferring method and the like.

As the anode material, in general, it is preferable to use the material having the large work function so as to smoothly perform hole injection into the organic material layer. As examples of the anode material that is capable of being used in the present invention, there are metal such as vanadium, chrome, copper, zinc, gold and the like or alloy thereof; metal oxides such as zinc oxides, indium oxides, indium tin oxides (ITO), indium zinc oxides (IZO) and the like; a combination of metal and oxides such as ZnO:Al or $SnO_2$:Sb; conductive polymers such as poly(3-methylthiophene), poly[3,4-(ethylene-1,2-dioxy) compound] (PEDT), polypyrrole and polyaniline, but they are not limited thereto.

As the cathode material, in general, it is preferable to use the material having the small work function so as to smoothly perform electron injection into the organic material layer. As detailed examples of the cathode material, there are metal such as magnesium, calcium, sodium, potassium, titanium, indium, yttrium, lithium, gadolinium, aluminum, silver, tin, and lead or an alloy thereof; a multilayered structure material such as LiF/Al or $LiO_2$/Al, but they are not limited thereto.

The hole injection material is a material that is capable of well receiving holes from the anode at a low voltage, and it is preferable that the HOMO (highest occupied molecular orbital) of the hole injection material is a value between the work function of the anode material and the HOMO of the organic material layer around them. As detailed examples of the hole injection material, there are metal porphyrine, oligo thiophene, arylamine-based organic material, hexanitrile-hexaazatriphenylene-based organic material, quinacridone-based organic material, perylene-based organic material, anthraquinone and polyaniline and poly thiophene-based conductive polymers, but they are not limited thereto.

The hole transport material is a material that receives the holes from the anode or the hole injection layer and transfers them to the light emitting layer, and it is preferable to use the material having the large mobility to the holes. As detailed examples thereof, there are arylamine-based organic material, a conductive polymer, and a block copolymer in which a conjugate portion and a nonconjugate portion are simultaneously included, but they are not limited thereto.

The light emitting material is a material that receives and combines the holes and the electrons from the hole transport layer and the electron transport layer, such that light at a range of visible rays is emitted, and it is preferable to use the material having excellent photon efficiency to fluorescence or phosphorescence. As detailed examples thereof, there are a 8-hydroxy-quinoline aluminum complex ($Alq_3$); a carbazole-based compound; a dimerized styryl compound; BAlq; 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but they are not limited thereto.

The electron transport material is a material that well receives the electrons from the cathode and transfers them to the light emitting layer, and it is preferable to use the material having the large mobility to the electrons. As detailed examples thereof, there are a 8-hydroxyquinoline Al complex; a complex including $Alq_3$; an organic radical compound; a hydroxyflavone metal complex and the like, but they are not limited thereto.

The organic light emitting device according to the present invention may be a top emission type, a bottom emission type, or a both-sided emission type according to the used material.

MODE FOR INVENTION

Hereinafter, preparation methods of compounds represented by Formula 1 and a method for manufacturing an organic electronic device using the same and performance thereof will be described in detail through Examples. However, the following Examples are set forth to illustrate but are not to be construed to limit the present invention.

EXAMPLE

Preparation Example 1

Preparation of the compound represented by Formula 1-1

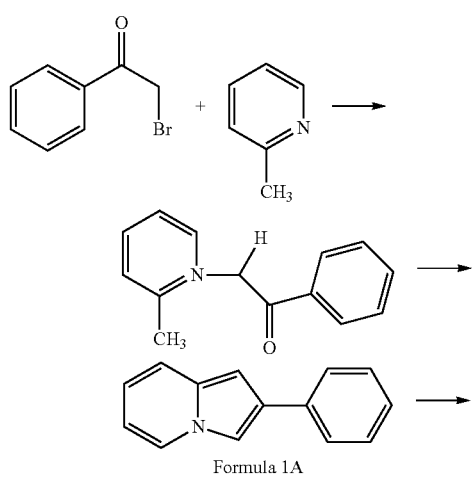

Formula 1A

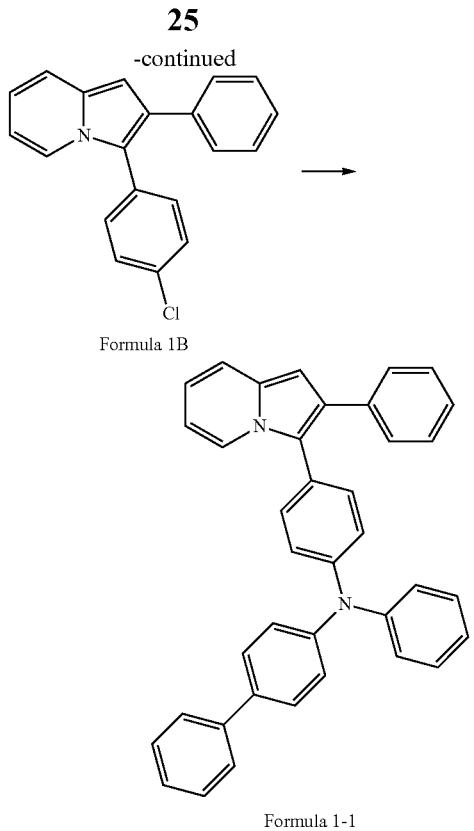

Formula 1B (top)

Formula 1-1 (bottom)

1) Preparation of Formula 1A 2-bromoacetophenone (25.4 g, 127.6 mmol), and 2-picoline (11.9 g, 127.6 mmol) were put into 150 ml of toluene, and refluxed under the nitrogen atmosphere for 3 hours. The product generated after being cooled to room temperature was filtered. The filtered product was agitated in $K_2CO_3$ (aq) at 80° C. The product generated after being cooled to room temperature was filtered and dried to obtain Formula 1A (20.3 g, yield 82%).

MS: $[M+H]^+$=194

2) Preparation of Formula 1B

Formula 1A (5.0 g, 25.87 mmol), and 1-bromo-4-chlorobenzene (5.94 g, 31.05 mmol) were dissolved in 100 ml of NMP, $H_2O$ 1 ml, KOAc (5.0 g, 51.74 mmol), and $PdCl_2(PPh_3)_2$ (0.95 g, 1.29 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 1B (7.5 g, yield 95%).

MS: $[M+H]^+$=304

3) Preparation of Formula 1-1

Formula 1B (7.5 g, 24.69 mmol), and N-phenyl-biphenylamine (6.6 g, 27.15 mmol) were dissolved in 150 ml of xylene, sodium-tertiary-botoxide (3.56 g, 37 mmol), and $Pd[P(t-Bu)_3]_2$ (0.13 g, 0.247 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 1-1 (7.3 g, yield 57%).

MS: $[M+H]^+$=513

Preparation Example 2

Preparation of the Compound Represented by Formula 1-2

Formula 1B (7.5 g, 24.69 mmol), and N-biphenyl-1-naphtylamine (8.0 g, 27.15 mmol) were dissolved in 150 ml of xylene, sodium-tertiary-botoxide (3.56 g, 37 mmol), and $Pd[P(t-Bu)_3]_2$ (0.13 g, 0.247 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 1-2 (6.8 g, yield 49%).

MS: $[M+H]^+$=563

Preparation Example 3

Preparation of the Compound Represented by Formula 1-3

Formula 1B (7.5 g, 24.69 mmol), and bisbiphenylamine (8.73 g, 27.15 mmol) were dissolved in 150 ml of xylene, sodium-tertiary-botoxide (3.56 g, 37 mmol), and $Pd[P(t-Bu)_3]_2$ (0.13 g, 0.247 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 1-3 (7.3 g, yield 44%).

MS: $[M+H]^+$=665

Preparation Example 4

Preparation of the Compound Represented by Formula 1-5

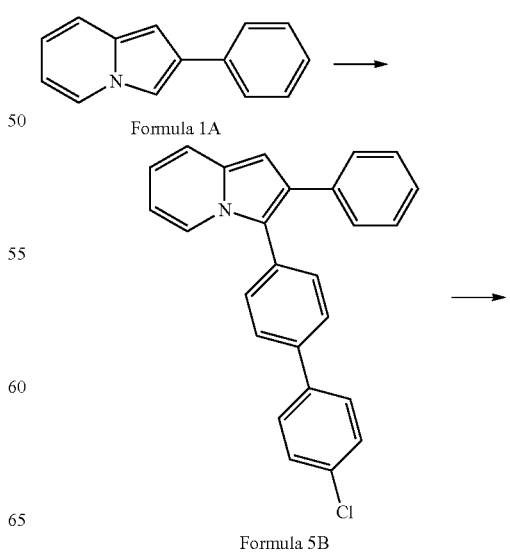

Formula 1A (top)

Formula 5B (bottom)

-continued

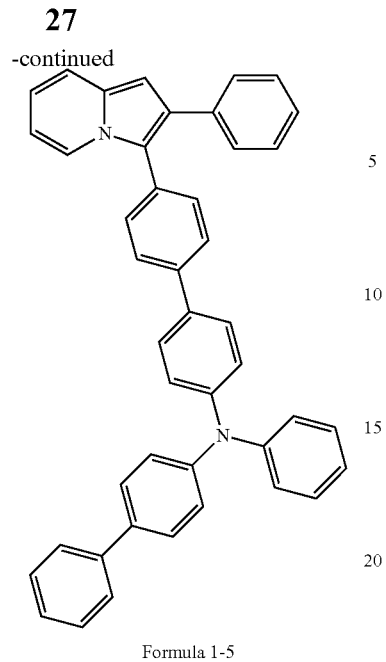

Formula 1-5

1) Preparation of Formula 5B

Formula 1A (5.0 g, 25.87 mmol), and 1-bromo-4-chlorobiphenyl (8.3 g, 31.05 mmol) were dissolved in 100 ml of NMP, H$_2$O 1 ml, KOAc (5.0 g, 51.74 mmol), and PdCl$_2$(PPh$_3$)$_2$ (0.95 g, 1.29 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 5B (5.96 g, yield 60%).

MS: [M+H]$^+$=380

2) Preparation of Formula 1-5

Formula 5B (5.96 g, 15.69 mmol), and N-phenyl-biphenylamine (5.55 g, 17.26 mmol) were dissolved in 150 ml of xylene, sodium-tertiary-botoxide (2.26 g, 23.53 mmol), and Pd[P(t-Bu)$_3$]$_2$ (0.08 g, 0.157 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 1-5 (4.9 g, yield 47%).

MS: [M+H]$^+$=665

Preparation Example 5

Preparation of the Compound Represented by Formula 1-9

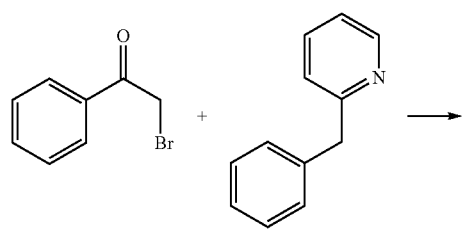

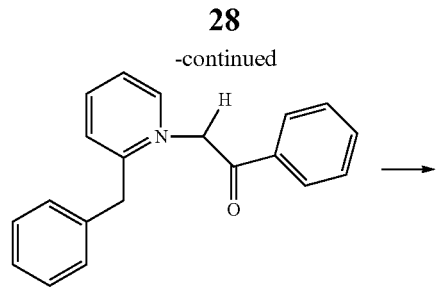

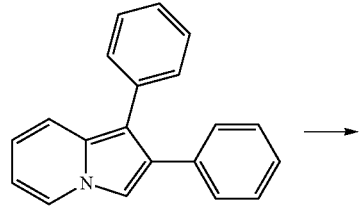

Formula 9A

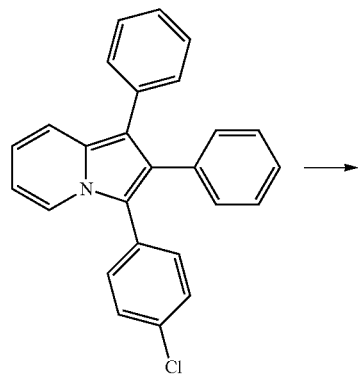

Formula 9B

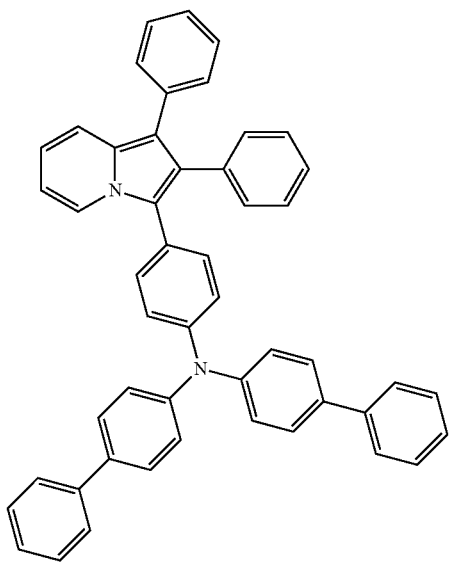

Formula 1-9

1) Preparation of Formula 9A 2-bromoacetophenone (10 g, 50.24 mmol), and 2-benzylpyridine (8.5 g, 50.24 mmol) were put into 150 ml of toluene, and refluxed for 3 hours under the nitrogen atmosphere. The product generated after being cooled to room temperature was filtered. The filtered product was agitated in K$_2$CO$_3$(aq) at 80° C. The product generated after being cooled to room temperature was filtered and dried to obtain Formula 9A (8.7 g, yield 64%).

MS: [M+H]$^+$=270

2) Preparation of Formula 9B

Formula 9A (5.0 g, 18.56 mmol), and 1-bromo-4-chlorobenzene (4.3 g, 22.27 mmol) were dissolved in 100 ml of NMP, $H_2O$ 0.67 ml, KOAc (3.64 g, 37.12 mmol), and $PdCl_2(PPh_3)_2$ (0.68 g, 0.928 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 9B (5.9 g, yield 83%).

MS: $[M+H]^+=380$

3) Preparation of Formula 1-9

Formula 9B (7.39 g, 19.45 mmol), and bisbiphenylamine (6.87 g, 21.4 mmol) were dissolved in 150 ml of xylene, sodium-tertiary-botoxide (2.8 g, 29.17 mmol), and $Pd[P(t-Bu)_3]_2$ (0.09 g, 0.194 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 1-9 (7.3 g, yield 56%).

MS: $[M+H]^+=665$

Preparation Example 6

Preparation of the Compound Represented by Formula 1-11

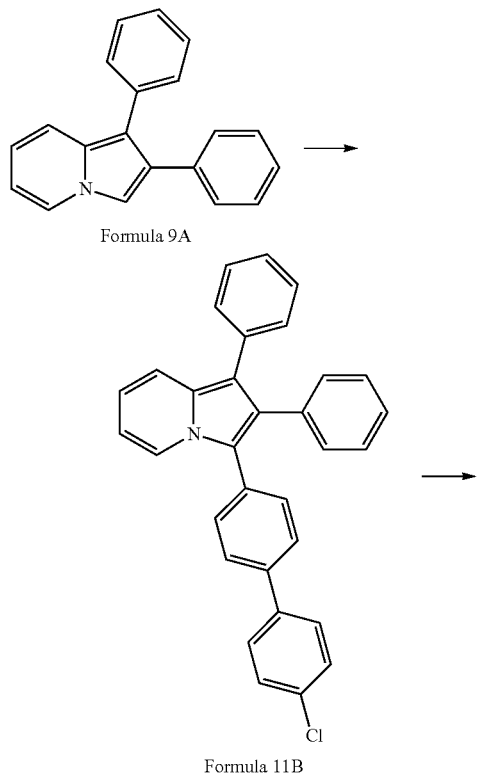

Formula 9A

Formula 11B

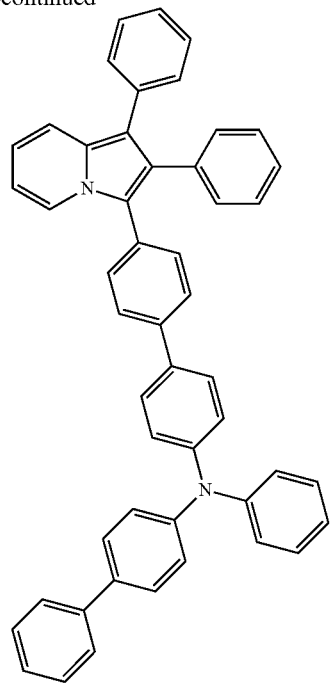

Formula 1-11

1) Preparation of Formula 11B

Formula 9A (5.0 g, 18.56 mmol), and 1-bromo-4-chlorobiphenyl (5.96 g, 22.27 mmol) were dissolved in 100 ml of NMP, $H_2O$ 0.67 ml, KOAc (3.64 g, 37.12 mmol), and $PdCl_2(PPh_3)_2$ (0.68 g, 0.928 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 11B (6.0 g, yield 70%).

MS: $[M+H]^+=456$

2) Preparation of Formula 1-11

Formula 11B (6.0 g, 13.16 mmol), and N-phenyl-biphenylamine (3.54 g, 14.47 mmol) were dissolved in 150 ml of xylene, sodium-tertiary-botoxide (1.89 g, 19.74 mmol), and $Pd[P(t-Bu)_3]_2$ (0.067 g, 0.13 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 1-11 (5.1 g, yield 58%).

MS: $[M+H]^+=665$

Preparation Example 7

Preparation of the Compound Represented by Formula 1-12

Formula 11B (6.0 g, 13.16 mmol), and bisbiphenylamine (4.65 g, 14.47 mmol) were dissolved in 150 ml of xylene, sodium-tertiary-botoxide (1.89 g, 19.74 mmol), and $Pd[P(t-Bu)_3]_2$ (0.067 g, 0.13 mmol) were added thereto, and refluxed for 5 hours under the nitrogen atmosphere. Distilled water was put into the reaction solution, the termination of the reaction was carried out, and the organic layer was extracted. After the column separation was carried out with normal-hexane/tetrahydrofurane=10/1 solvent, it was agitated in petroleum ether, and dried under vacuum to manufacture Formula 1-12 (6.5 g, yield 66%).

MS: [M+H]$^+$=741

Example 1

A glass substrate (Corning 7059 glass) on which a thin film of ITO (indium tin oxide) was coated to a thickness of 1,000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using in order of isopropyl alcohol, acetone and methanol as a solvent, and the resultant product was dried.

On the ITO transparent electrode thus prepared, hexanitrile hexaazatriphenylene was coated to thicknesses of 500 Å by thermal vacuum deposition to form a hole injection layer. After the Structural Formula 1-1 (400 Å) that was the material transporting the holes and synthesized in the above Preparation Example was deposited under the vacuum state thereon, the host H1 and the dopant D1 compound were deposited under the vacuum state in a thickness of 300 Å as a light emitting layer. Thereafter, the E1 compound (300 Å) was deposited by heating under the vacuum as an electron injection and transport layer. On the electron injection and transport layer, lithium fluoride (LiF) in a thickness of 12 Å and aluminum in a thickness of 2,000 Å were subsequently deposited to form a cathode, thereby manufacturing the organic light emitting device.

In the above process, the deposition speed of the organic substance was maintained at 1 Å/sec, that of lithium fluoride was maintained at 0.2 Å/sec, and that of aluminum was maintained at 3 to 7 Å/sec.

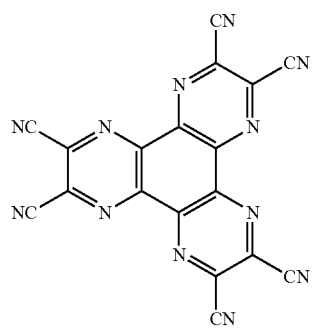

[hexanitrile hexaazatriphenylene]

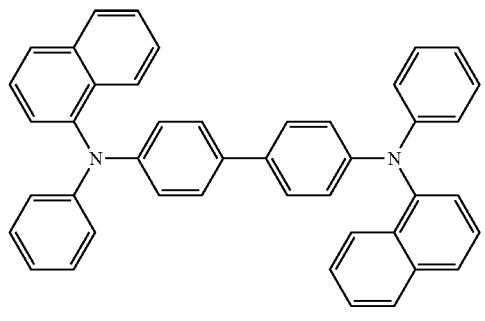

[NPB]

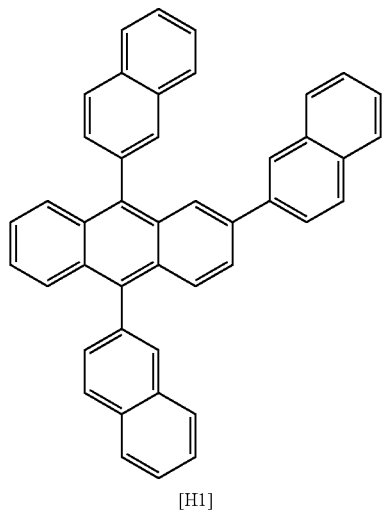

[H1]

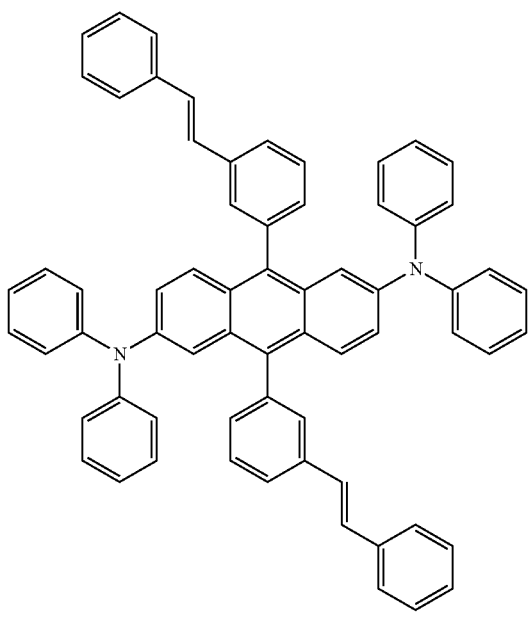

[D1]

-continued

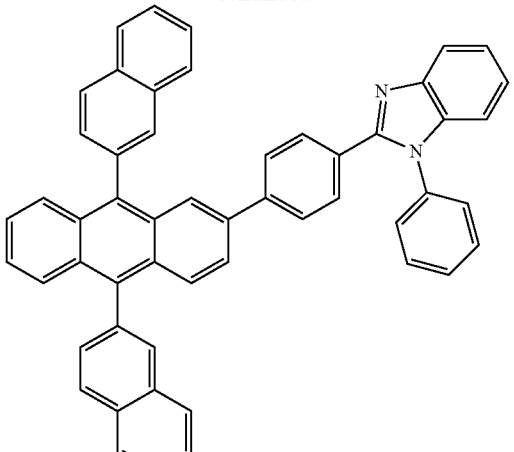

[E1]

Example 2

The same experiment was conducted, except that Formula 1-2 was used instead of Formula 1-1 that was synthesized in Preparation Example as the hole transport layer in Example 1.

Example 3

The same experiment was conducted, except that Formula 1-3 was used instead of Formula 1-1 that was synthesized in Preparation Example as the hole transport layer in Example 1.

Example 4

The same experiment was conducted, except that Formula 1-5 was used instead of Formula 1-1 that was synthesized in Preparation Example as the hole transport layer in Example 1.

Example 5

The same experiment was conducted, except that Formula 1-9 was used instead of Formula 1-1 that was synthesized in Preparation Example as the hole transport layer in Example 1.

Example 6

The same experiment was conducted, except that Formula 1-11 was used instead of Formula 1-1 that was synthesized in Preparation Example as the hole transport layer in Example 1.

Example 7

The same experiment was conducted, except that Formula 1-12 was used instead of Formula 1-1 that was synthesized in Preparation Example as the hole transport layer in Example 1.

Comparative Example

The same experiment was conducted, except that NPB was used instead of Formula 1-1 that was synthesized in Preparation Example as the hole transport layer in Example 1.

Like Examples 1 to 7 and Comparative Example, the test results of the organic light emitting device manufactured by using each compound as the hole transport layer material are described in the following Table 1.

TABLE 1

| Experimental Example (100 mA/cm²) | HTL material | Voltage (V) | Current efficiency (cd/A) | Color coordinate (x, y) |
|---|---|---|---|---|
| Comparative Example | NPB | 8.18 | 26.59 | (0.314, 0.650) |
| Example 1 | Formula 1-1 | 8.21 | 27.63 | (0.317, 0.662) |
| Example 2 | Formula 1-2 | 8.28 | 28.11 | (0.318, 0.671) |
| Example 3 | Formula 1-3 | 8.22 | 28.21 | (0.317, 0.661) |
| Example 4 | Formula 1-5 | 8.29 | 28.32 | (0.318, 0.663) |
| Example 5 | Formula 1-9 | 8.29 | 27.98 | (0.318, 0.667) |
| Example 6 | Formula 1-11 | 8.31 | 28.12 | (0.318, 0.668) |
| Example 7 | Formula 1-12 | 8.32 | 28.34 | (0.319, 0.667) |

A compound derivative of Formula according to the present invention may act as a hole injection, a hole transport, an electron injection and transport, or a light emitting material in an organic light emitting device and an organic electronic device, and the device according to the present invention shows excellent properties in terms of efficiency, a driving voltage, and stability.

The invention claimed is:

1. A compound represented by the following Formula 1:

[Formula 1]

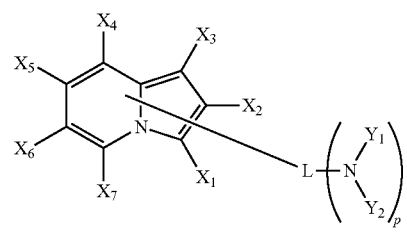

wherein

L is a connection group connected to at least one A, and substituted or unsubstituted $C_6$ to $C_{60}$ arylene group, substituted or unsubstituted fluorene group, or substituted or unsubstituted $C_3$ to $C_{60}$ heteroarylene group, $Y_1$ and $Y_2$ are the same as or different from each other, and each independently unsubstituted $C_6$ to $C_{60}$ aryl group, $C_6$ to $C_{60}$ aryl group substituted with at least one substituent selected from the group consisting of deuterium; halogen; cyano group; nitro group; hydroxyl group; $C_1$ to $C_{50}$ alkyl group; $C_1$ to $C_{50}$ alkoxy group; $C_3$ to $C_{50}$ cycloalkyl group; $C_3$ to $C_{60}$ heterocycloalkyl group; $C_6$ to $C_{60}$ aryl group; thiophene group, furan group, pyrrole group, imidazole group, thiazole group, oxazol group, oxadiazol group, triazol group, pyridyl group, pyradazine group, quinolinyl group, isoquinoline group, acridyl group, arylamine group, fluorene group, and silicon group, unsubstituted $C_3$ to $C_{60}$ heteroaryl group, or $C_3$ to $C_{60}$ heteroaryl group substituted with at least one substituent selected from the group consisting of deuterium; halogen; cyano group; nitro group; hydroxyl group; $C_1$ to $C_{50}$ alkyl group; $C_1$ to $C_{50}$ alkoxy group; $C_3$ to $C_{50}$ cycloalkyl group; $C_3$ to $C_{60}$ heterocycloalkyl group; $C_6$ to $C_{60}$ aryl group; thiophene group, furan group, pyrrole group, imidazole group, thiazole group, oxazol group, oxadiazol group, triazol group, pyridyl group, pyradazine group, quinolinyl group, isoquinoline group, acridyl group, arylamine group, fluorene group, and silicon group, p is an integer in the range of 1 to 10, at least one of $X_1$ to $X_7$ is connected to L, and the remains are each independently hydrogen; deuterium; halogen; cyano group; nitro group; hydroxyl group; substituted or unsubstituted $C_1$ to $C_{50}$ alkyl group; substituted or unsubstituted $C_1$ to $C_{50}$ alkoxy group; substituted or unsubstituted $C_3$ to $C_{50}$ cycloalkyl group; substituted or unsubstituted $C_3$ to $C_{60}$ heterocycloalkyl group; substituted or unsubstituted $C_6$ to $C_{60}$ aryl group; substituted or unsubstituted $C_3$ to $C_{60}$ heteroaryl group; substituted or unsubstituted arylamine group; or substituted or unsubstituted silicon group.

2. The compound according to claim 1, wherein the aryl group of Formula 1 is phenyl group, biphenyl, terphenyl group, stilben, naphthyl group, anthracenyl group, phenanthrene group, pyrenyl group, perylenyl group, or cryxenyl group.

3. The compound according to claim 1, wherein the heteroaryl group of Formula 1 is thiophene group, furan group, pyrrole group, imidazole group, thiazole group, oxazol group, oxadiazol group, triazol group, pyridyl group, pyradazine group, quinolinyl group, isoquinoline group, or acridyl group.

4. The compound according to claim 1, wherein

of Formula 1 is selected from the following Formulas:

1

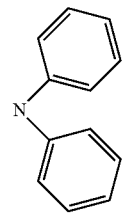

2

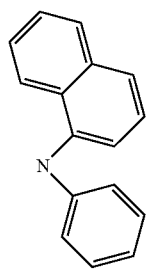

3

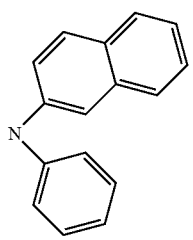

-continued

4

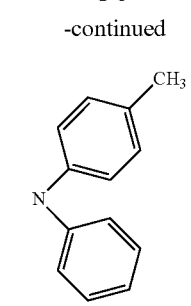

5

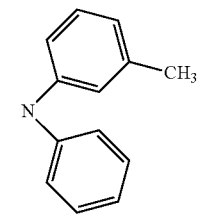

6

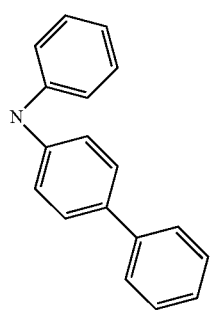

7

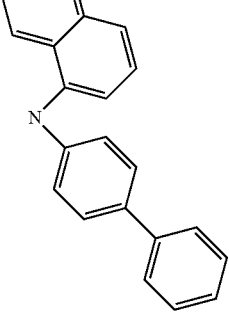

8

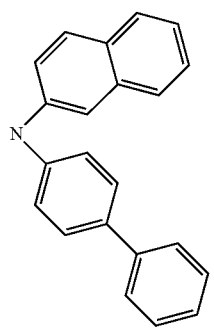

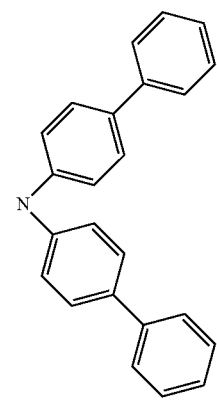
9
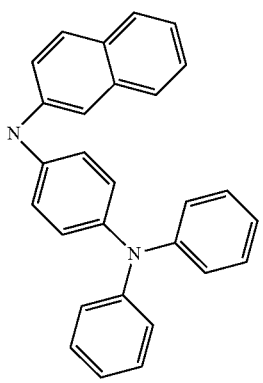
10
11
12
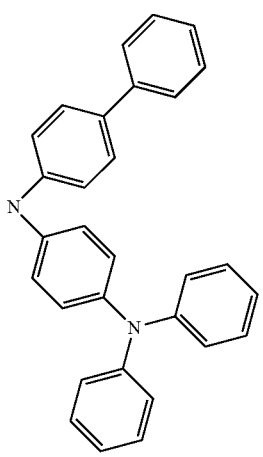
13
14
15
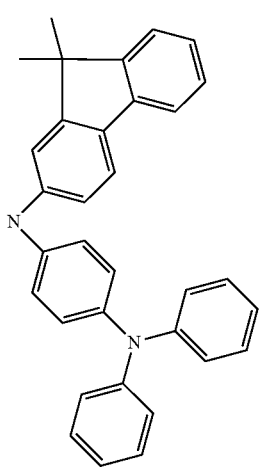

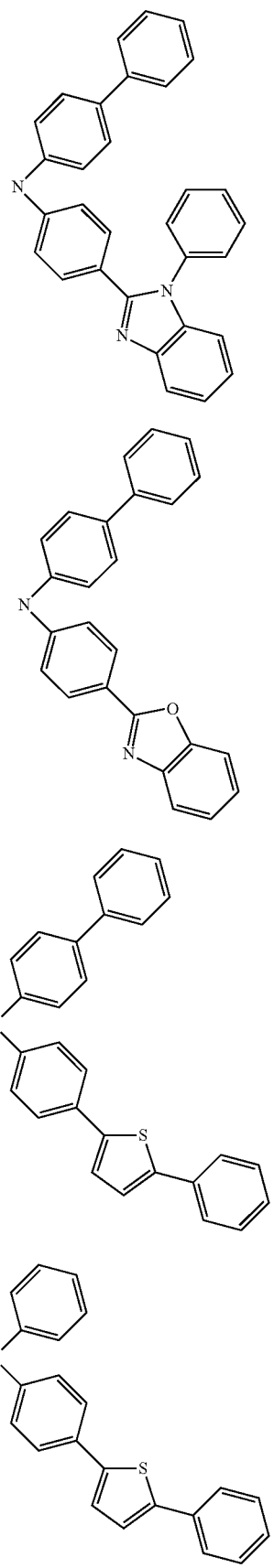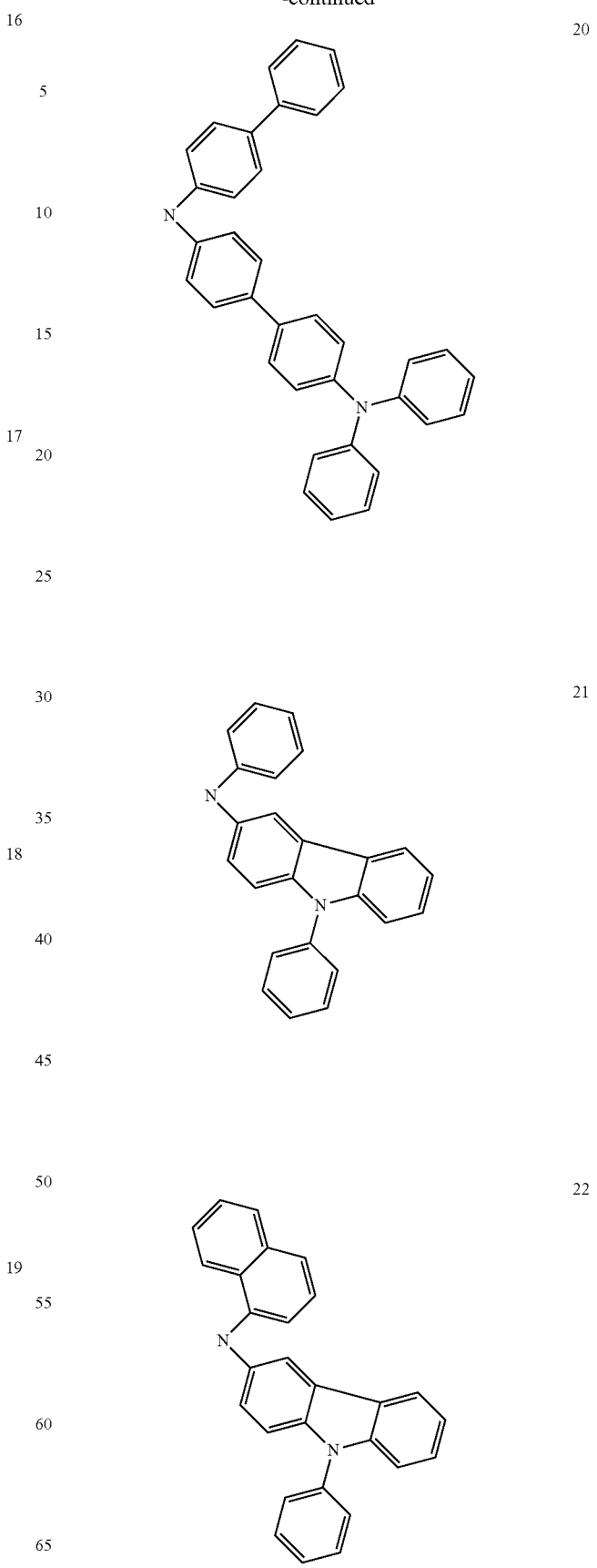

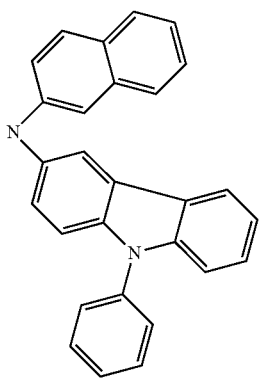
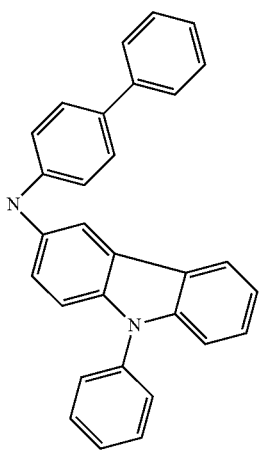
5. The compound according to claim 1, wherein the fluorene group of Formula 1 is selected from the following structures:
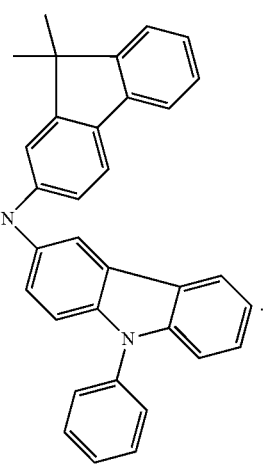
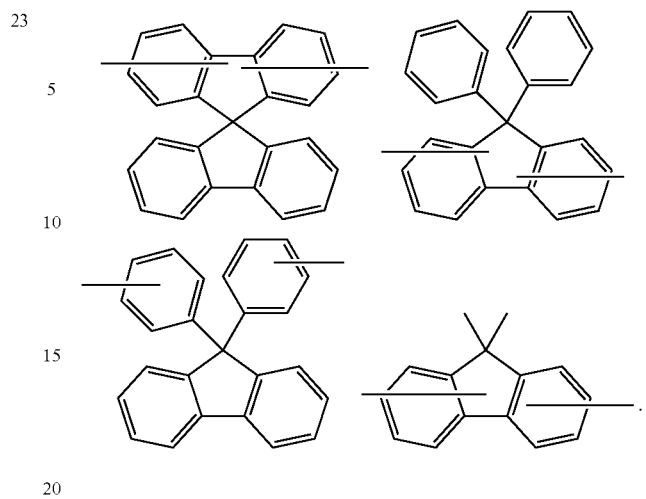
6. The compound according to claim 1, wherein the heteroarylene group of Formula 1 is selected from the following structures:
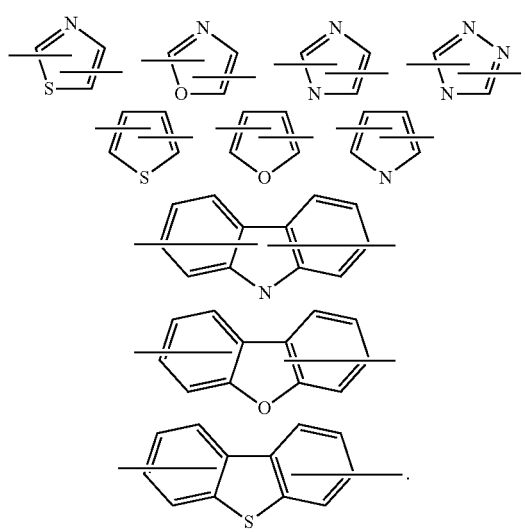
7. The compound according to claim 1, wherein the compound of Formula 1 is represented by the following Formulas:
Formula 1-1
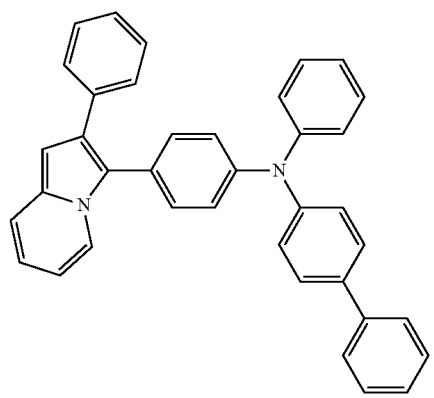

Formula 1-2
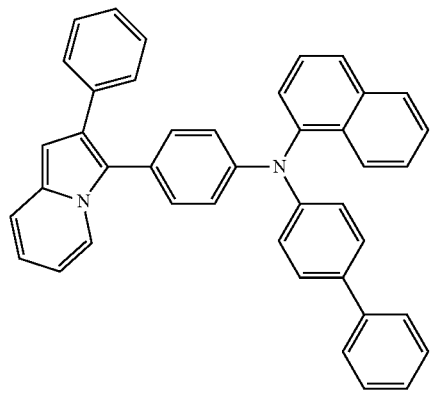
Formula 1-3
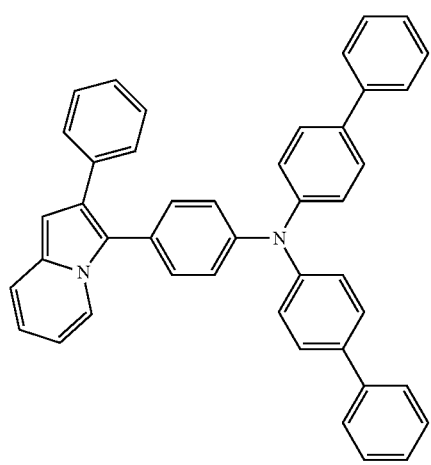
Formula 1-4
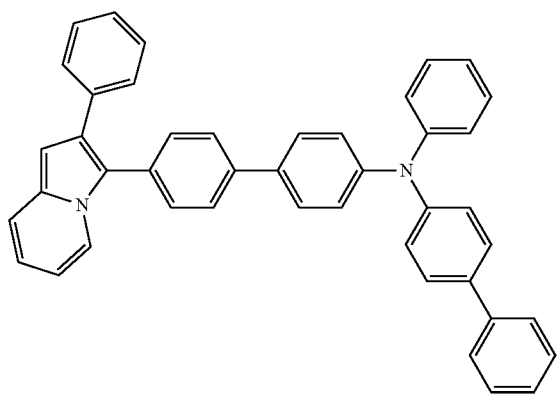
Formula 1-5
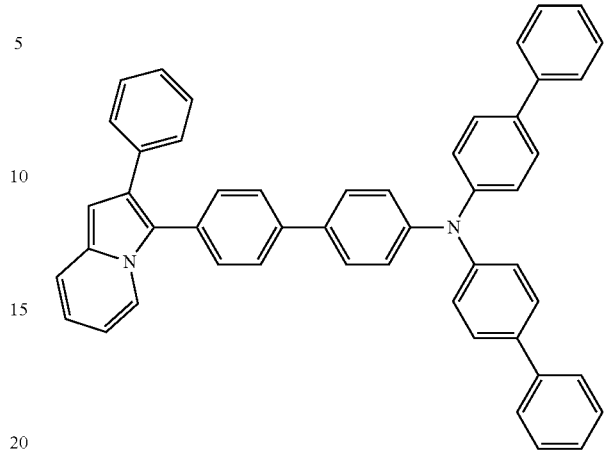
Formula 1-6
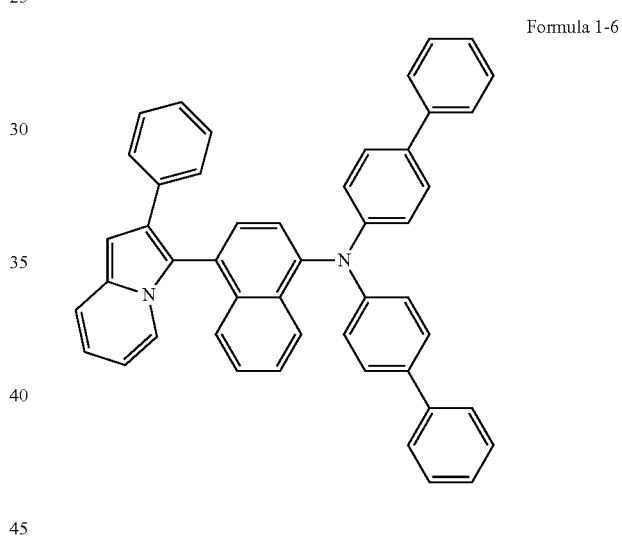
Formula 1-7
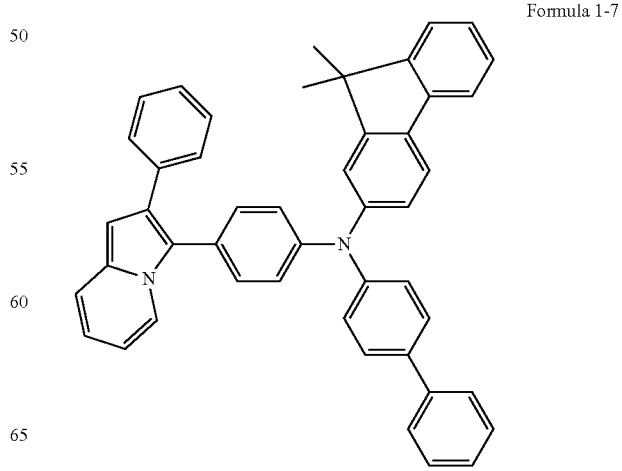

Formula 1-8
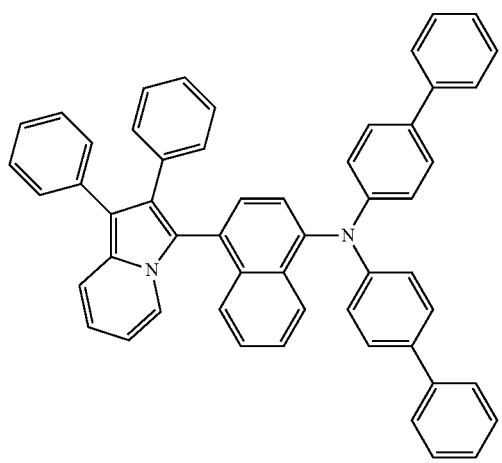
Formula 1-11
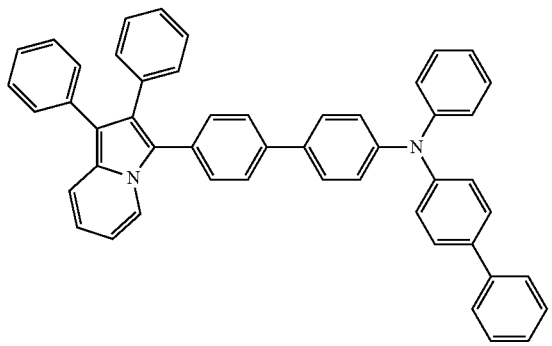
Formula 1-9
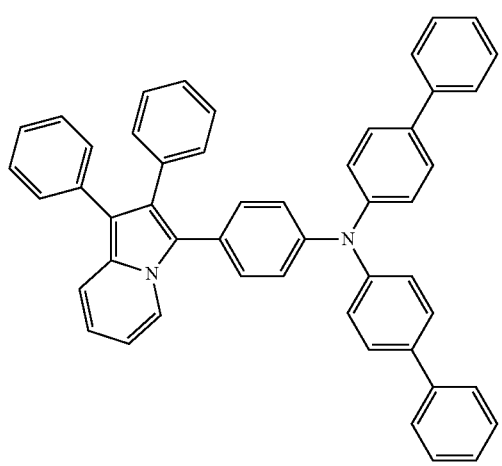
Formula 1-12
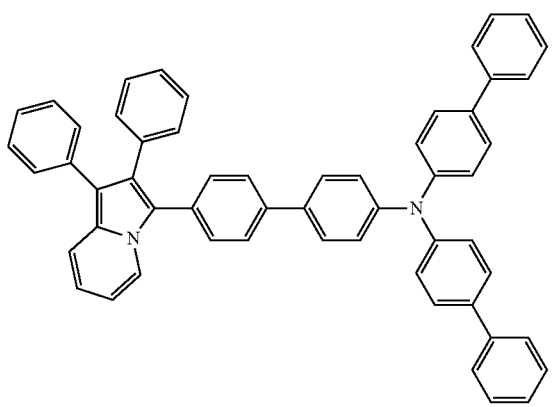
Formula 1-10
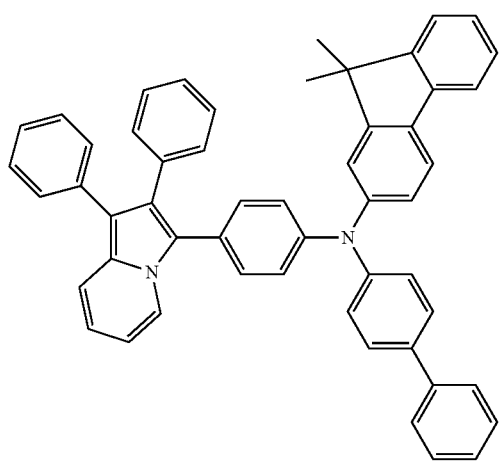
Formula 1-13
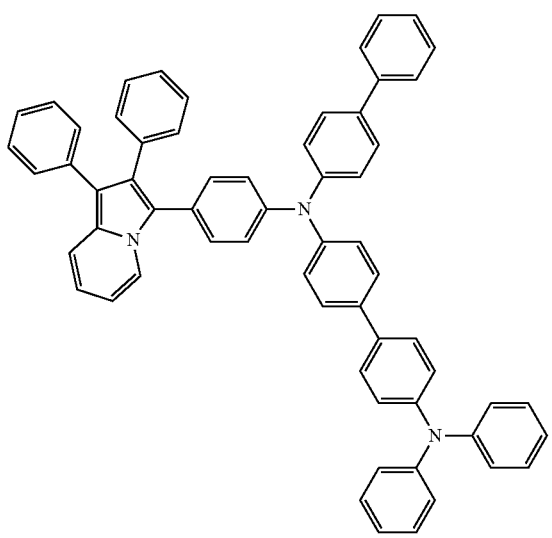

-continued
Formula 1-14
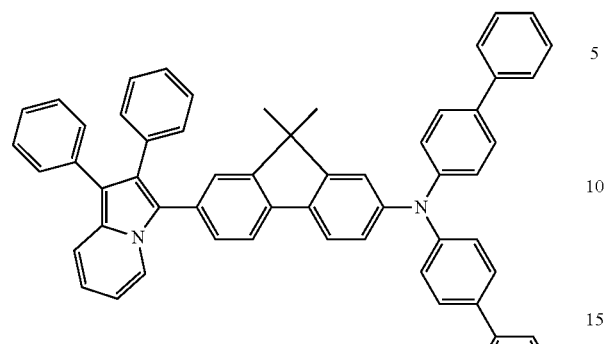
Formula 1-15
Formula 1-16
Formula 1-17
Formula 1-18
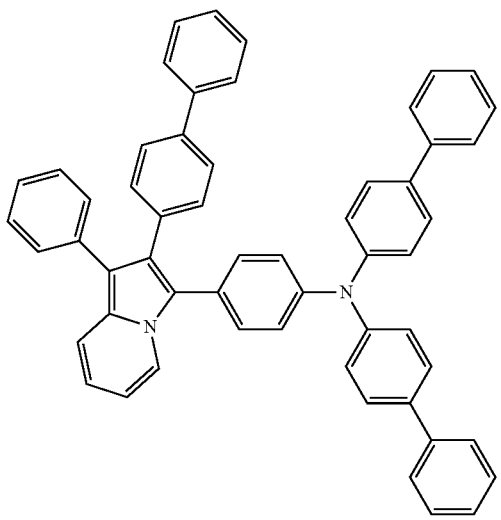
Formula 1-19
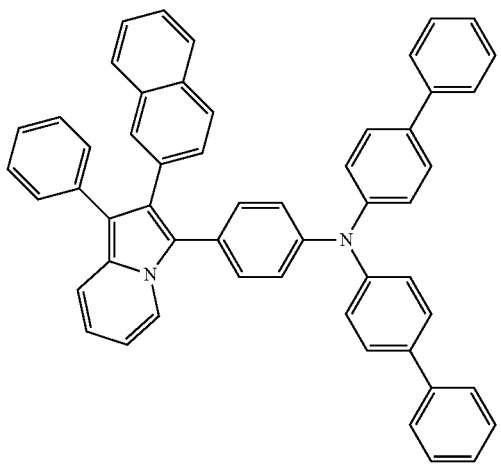
Formula 1-20
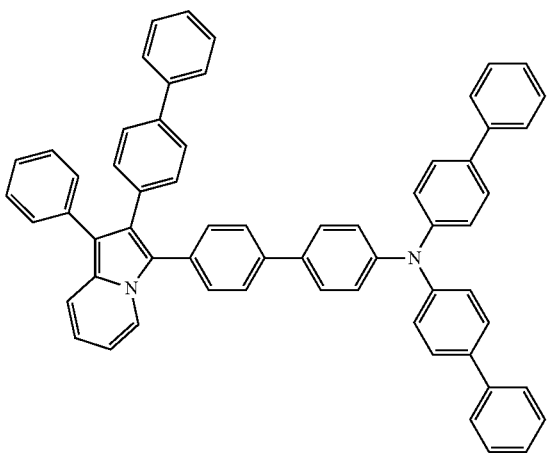

Formula 1-21
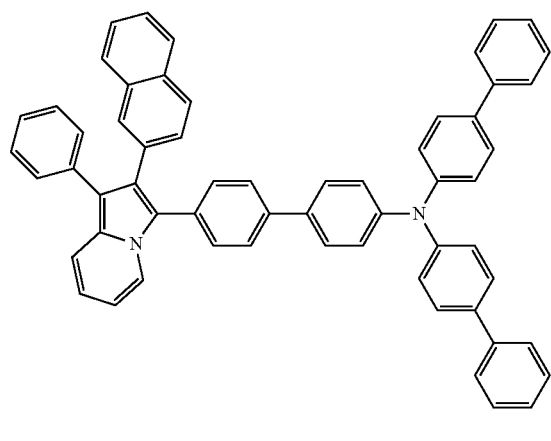
Formula 1-24
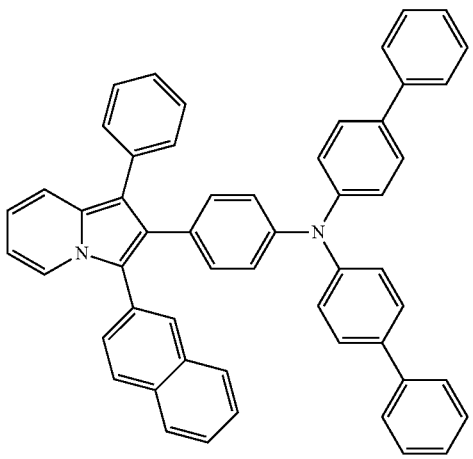
Formula 1-22
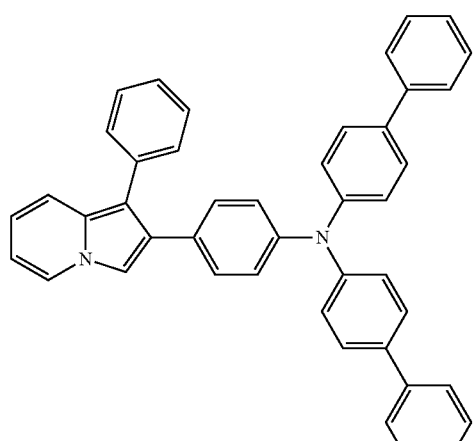
Formula 1-25
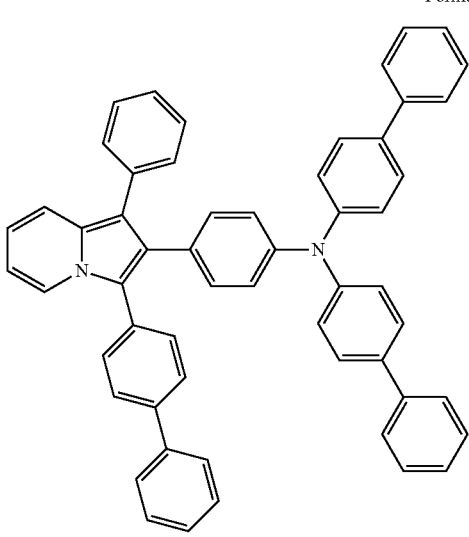
Formula 1-23
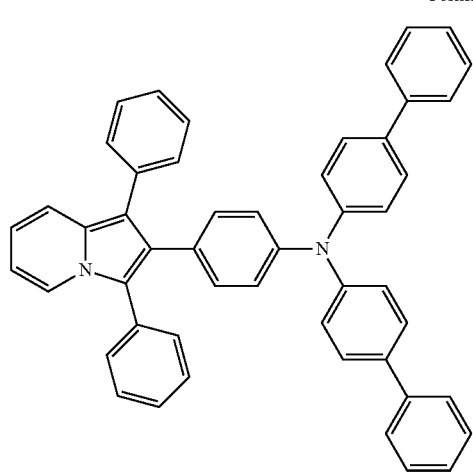
Formula 1-26
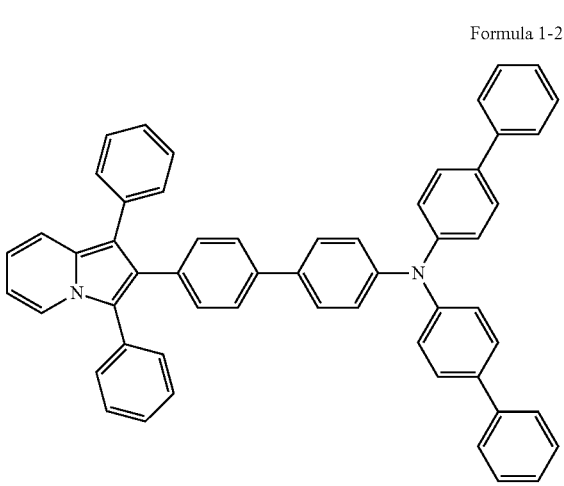

-continued

Formula 1-27
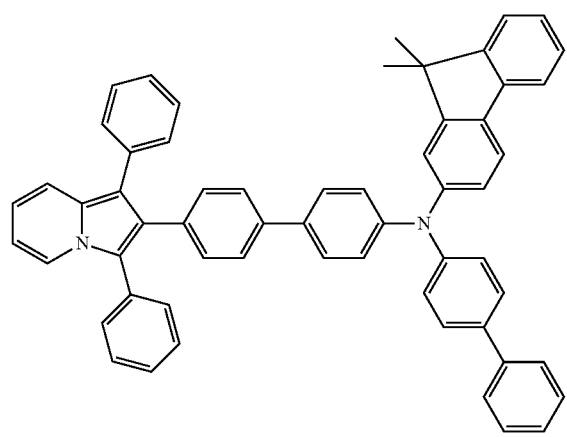

Formula 1-28
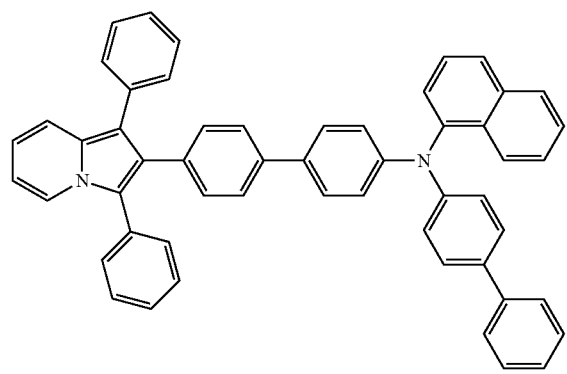

Formula 1-29
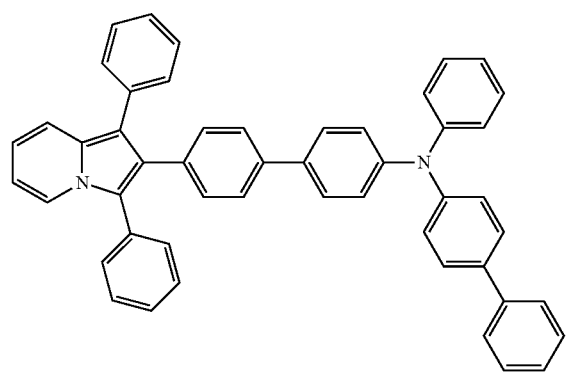

-continued

Formula 1-30
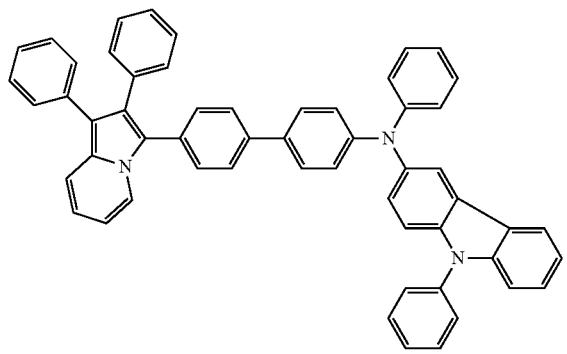

Formula 1-31
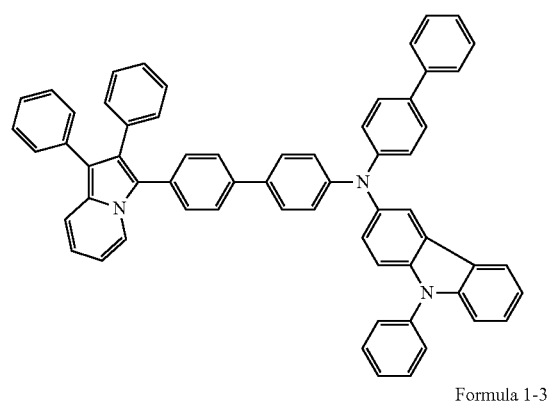

Formula 1-32
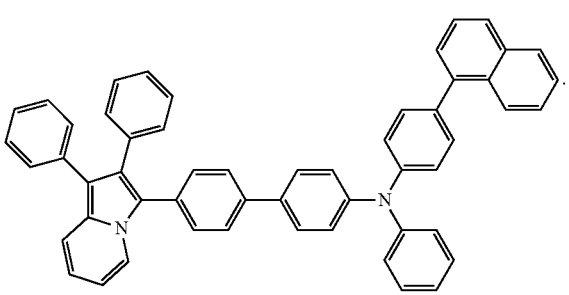

8. An organic light emitting device comprising:
a first electrode,
one or more organic material layer including a light emitting layer, and
a second electrode in a layer form,
wherein one or more layers of the organic material layers include the compound of claim 1.

9. The organic light emitting device according to claim 8, wherein the light emitting layer includes red, green, blue or white phosphorescent or fluorescent dopant.

10. The organic light emitting device according to claim 9, wherein the phosphorescent dopant is an organic metal compound that includes one or more elements that are selected from the group consisting of Ir, Pt, Os, Ti, Zr, Hf, Eu, Tb and Tm.

* * * * *